US008822159B2

(12) United States Patent
Caprioli et al.

(10) Patent No.: US 8,822,159 B2
(45) Date of Patent: Sep. 2, 2014

(54) METHOD FOR DIFFERENTIATING SPITZ NEVI FROM SPITZOID MALIGNANT MELANOMA

(71) Applicant: Vanderbilt University, Nashville, TN (US)

(72) Inventors: Richard Caprioli, Brentwwod, TN (US); Erin H. Seeley, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/757,345

(22) Filed: Feb. 1, 2013

(65) Prior Publication Data

US 2014/0044673 A1  Feb. 13, 2014

Related U.S. Application Data

(60) Provisional application No. 61/593,604, filed on Feb. 1, 2012.

(51) Int. Cl.
*C12Q 1/68* (2006.01)
(52) U.S. Cl.
USPC .......................................... 435/6.14
(58) Field of Classification Search
USPC .......................... 435/6.14; 382/128
IPC ........................................ C12Q 1/6886
See application file for complete search history.

(56) References Cited

U.S. PATENT DOCUMENTS 6,261,775 B1* 7/2001 Bastian et al. ............... 435/6.14
2013/0149704 A1* 6/2013 Jewell et al. ................. 435/6.11

OTHER PUBLICATIONS

Lazova R. et al. Mass Specrometry—A Promising Method to Differentiate Spitz Nevi from Spitzoid Malignant Melanoma. American J of Dermatopathology 33(4)418, Jun. 2011.*
Munkberg J. Validation of Tandem MS Study Using Laser Microdissected Melanoma and Nevus Cells. Laboratory Investigation 91(2) Supp 1, p. 121A, #503, Feb. 2011.*
Lazova R. et al. Imaging MS A New and Promising Method to Differentiate Spitz Nevi from Spitzoid Malignant Melanomas. Am J Dermatopathology 34(1)82-90, Feb. 2012.*
Abaffy, T. et al. Differential Volatile Signature from Skin, Naevi and Melanoma. PLoS One, 5(11)e13813 1-12, Nov. 2010.*

Bastian et al., "Classifying melanocytic tumors based on DNA copy number changes", *Am J Pathol.*, 163:1765-1770, 2003.
Bastian el al., "Chromosomal gains and losses in primary cutaneous melanomas detected by comparative genomic hybridization", *Cancer Res.*, 58:2170-2175, 1998.
Bastian et al., "Molecular cytogenetic analysis of Spitz nevi shows clear differences to melanomas", *J Invest Dermatol.*, 113:1065-1069, 1999.
Bastian et al., "Mutations and copy number increase of HRAS in Spitz nevi with distincive histophalogical features", *Am J Pathol.*, 157:967-972, 2000.
Curtin et al., "Distinct sets of genetic alterations in melanoma", *N Engl J Med.*, 353:2135-2147, 2005.
Fullen et al., "BRAF and NRAS mutations in spitzoid melanocytic lesions", *Mod Pathol.*, 19:1324-1332, 2006.
Gaiser et al., "Classifying ambiguous melanocytic lesions with FISH and correlation with clinical long-term follow up", *Mod Pathol.*, 23:413-419, 2010.
Gill et al., "Genetic similarities between Spitz nevus and Spitzoid melanoma in children", Cancer, 101:2636-2640, 2004.
Hardesty et al. "Protein signatures for survival and recurrence in metastatic melanoma", *Journal of Proteomics*, 74:1002-1014, 2011.
Harvell el al., "High-resolution array-based comparative genomic hybridization for distinguishing paraffin-embedded Spitz nevi and melanomas", *Diagn Mol Pathol.*, 13:22-25, 2004.
Lazova et al., "Imaging mass sprectrometry—a new and promising method to differentiate spit nevi from spitzoid malignant melanomas", *Am J Dermatopathol.*, 34(1):82-90, 2012.
Lee et al., "Are all melanomas the same? Spitzoid melanoma is a distinct subtype of melanoma", *Cancer*, 106: 907-913, 2006.
Raskin et al., "Copy number variations and clinical outcome in atypical spitz tumors", *Am J Surg Pathol.*, 35:243-252, 2011.
van Engen-van Grunsven AC et al., "HRAS-mutated Spitz tumors: A subtype of Spitz tumors with distinct features", *Am J Surg Pathol.*, 34:1436-1441, 2010.
Abaffy et al., "Comparative analysis of volatile metabolomics signals from melanoma and benign skin: a pilot study", *Metabolomics*, 9:998-1008, 2013.
Jiang et al., "A non-invasive method for in vivo skin volatile compounds sampling", *Anal Chim Acta.*, 804:111-119, 2013. (Abstract Only).
Shirasu and Touhara, "The scent of disease: volatile organic compounds of the human body related to disease and disorder", *Journal of Biochemistry*, 150(3):257-266, 2011.

\* cited by examiner

*Primary Examiner* — Ralph Gitomer
(74) *Attorney, Agent, or Firm* — Parker Highlander PLLC

(57) ABSTRACT

The present invention provides for a mass spectrometry proteomic approach to distinguishing Spitz nevi from Spitzoid malignant melanoma. Histology directed mass spectral profiling allows for targeted analysis of sites of melanocytic lesion within formalin-fixed, paraffin embedded excisional biopsies. The classification system identified 5 peptide peaks, of which two have been identified as originating from vimentin and actin. A sensitivity and specificity for Spitz nevi of 97% and 90%, respectively, were achieved.

20 Claims, 9 Drawing Sheets

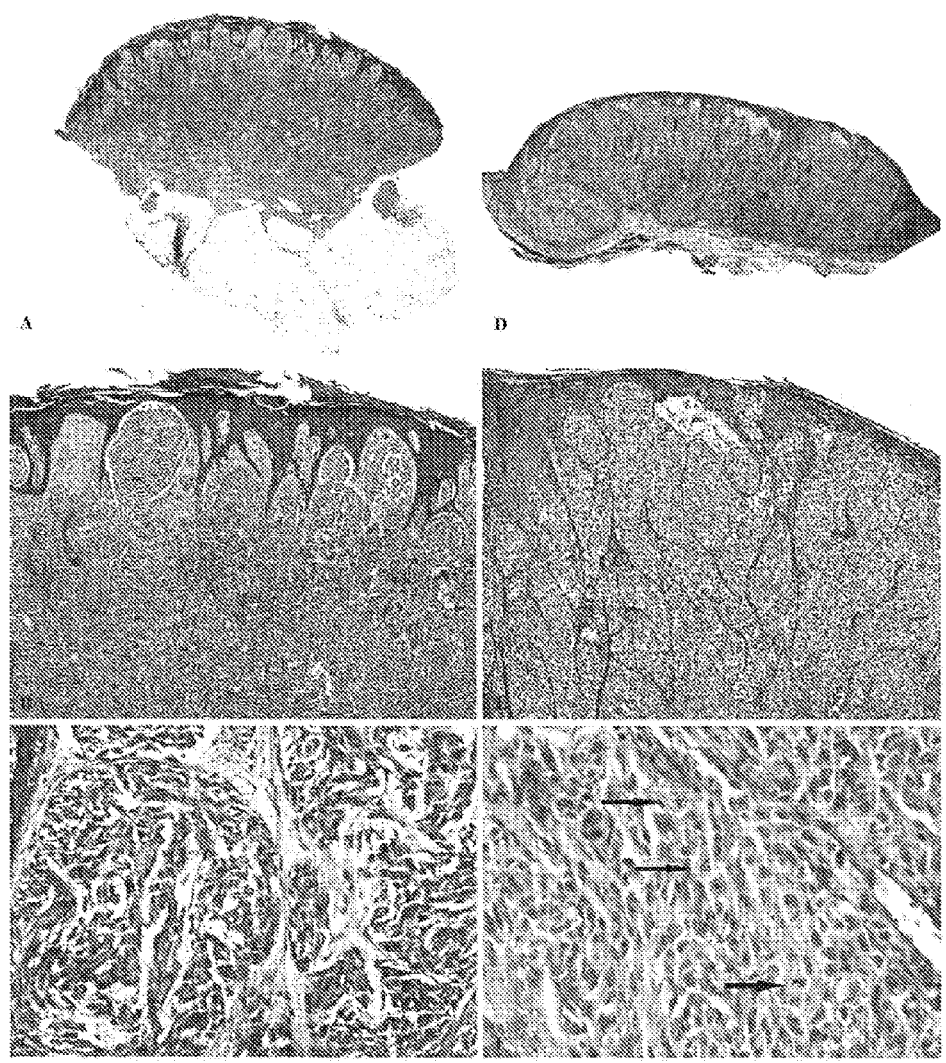
FIGS. 1A-F

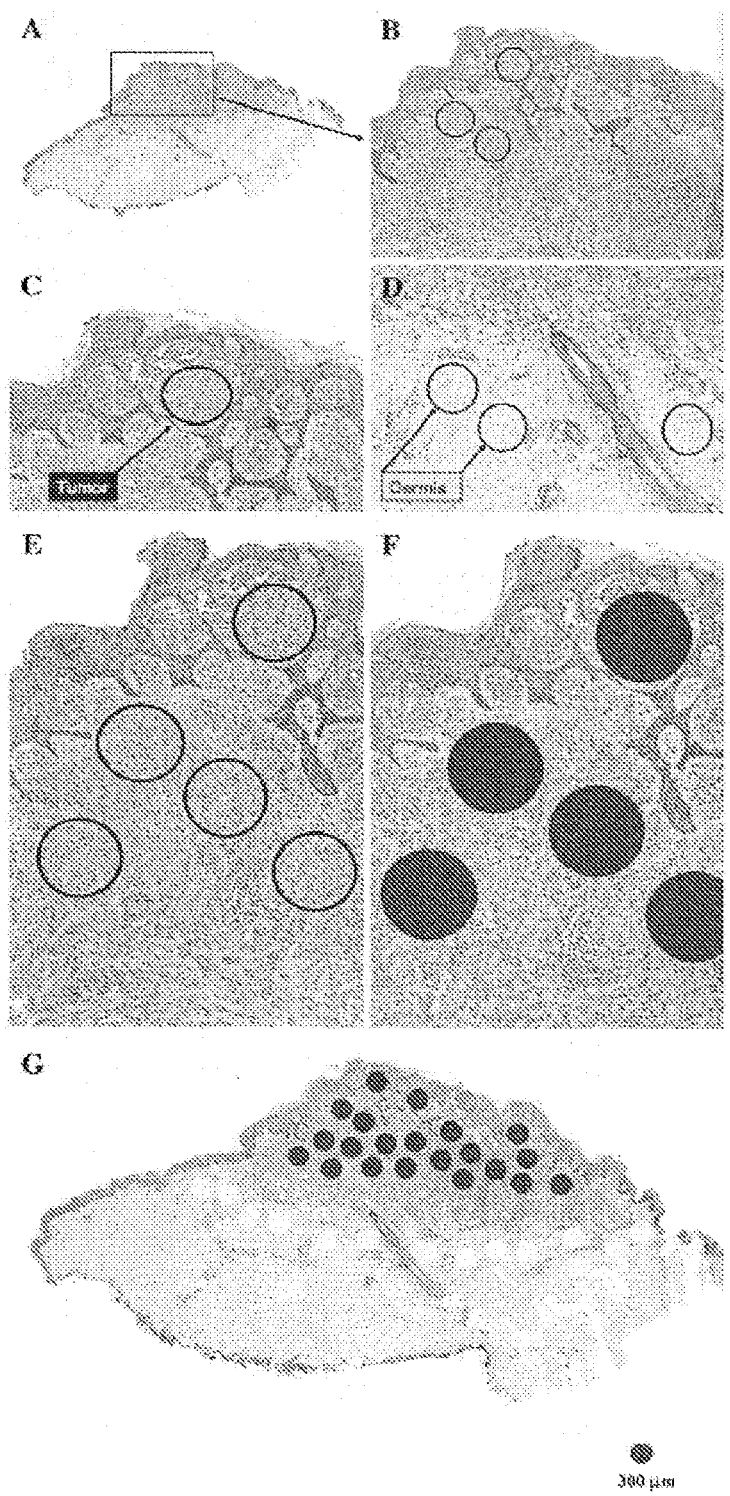
FIGS. 2A-G

METHOD FOR DIFFERENTIATING SPITZ NEVI FROM SPITZOID MALIGNANT MELANOMA

This application claims benefit of priority to U.S. Provisional Application Ser. No. 61/593,604, filed Feb. 1, 2012, the entire contents of which are hereby incorporated by reference.

This invention was made with government support under grant no. P50 CA121974 from the National Institutes of Health, and grant no. W81XWH-05-1-0179 from the Army/MRMC. The government has certain rights in the invention.

BACKGROUND OF THE INVENTION

1. Field of the Invention

The present invention relates generally to the fields of protein biology and oncology. More particularly, it concerns the classification of skin lesions based on mass spectrometry analysis of proteins from the lesions.

2. Description of Related Art

Ever since the first description of Spitz nevus (SN) by Sophie Spitz in 1948, pathologists and dermatopathologists in particular have been struggling with the distinction between SN and Spitzoid malignant melanoma (SMM). To diagnose a young child with melanoma, which has devastating consequences, and subject the child to surgery and chemotherapy is not a simple matter.

Spitzoid neoplasms are melanocytic lesions that include a spectrum ranging from completely benign "typical" SN to malignant melanomas that show "Spitzoid" features-SMM. The gold standard for diagnosing SN and differentiating it from SMM is histopathologic examination applying well established criteria. However, there are melanocytic lesions, which show conflicting histopathologic criteria and the distinction between a benign SN and SMM may be extremely difficult. These lesions are referred to as "atypical SN" or "atypical Spitzoid tumors/neoplasms." (Binder, et al. 1993; Barnhill, et al. 1995; Crotty, et al. 2002 and Ferrara, et al. 2005). There is a great interobserver variability and discordance even among expert dermatopathologists regarding Spitzoid neoplasms. (Barnhill, et al. 1995; Ackerman 1996; Barnhill, et al. 1999; Farmer, et al. 1996 and Rapini 1999). The presence of a gray area, in which it is extremely difficult or utterly impossible to distinguish between SN and SMM, continues to present a weak point in clinical diagnosis of these two closely related diseases.

Ancillary techniques such as comparative genomic hybridization and fluorescent in situ hybridization may be helpful. The majority of SN reveal no DNA copy number changes by comparative genomic hybridization. (Bastian, et al. 1999; Bastian, et al. 2003; Harvell, et al. 2004). Approximately 20% of SN show an isolated gain of chromosome 11p. (Bastian, et al. 1999). A subset of SN with 11p copy number increases has H-RAS mutation; however, that is extremely uncommon in cutaneous melanoma. (Bastian, 2000 and van Engen-van Grunsven, et al. 2010). In contrast, more than 95% of conventional melanomas show multiple chromosomal aberrations including gains and loses by comparative genomic hybridization. (Bastian, et al. 1998 and Curtin, et al. 2005).

B-RAF mutations have been found only in a small subset of SN, whereas the majority of conventional melanomas have B-RAF or N-RAS mutations. (Fullen, et al. 2006) Furthermore, activating hot spot mutations in the B-RAF, N-RAS, and H-RAS genes were not identified in SMM or SN (Lee, et al. 2006 and Gill, et al. 2004). These data suggest that SMM might be a distinct form of melanoma with unknown genes and/or signaling pathways involved in its development (Lee, et al. 2006; Gaiser, et al. 2010 and Raskin, et al. 2011).

Matrix-assisted laser desorption ionization (MALDI) imaging mass spectrometry (IMS) is a powerful method for analyzing metabolites, peptides and proteins, DNA segments, and lipids directly from tissue sections with spatial fidelity. Although gene expression is useful for distinguishing melanocytic nevi from melanomas, it does not always correlate with protein translation and does not account for posttranslational modification (PTM). However, both protein expression level and PTM state have fundamental effect on cellular function or dysfunction; therefore, it is more meaningful to analyze proteins and peptides that are involved in the development and progression of diseases, especially cancer. IMS has the ability to discover molecular signatures of diseases and cancer. These molecular signatures are typically comprised of 5-20 different proteins that together result in robust diagnostic patterns (Caprioli and Farmer, 1997 and Zimmerman, et al. 2008). IMS-based studies have been used to elucidate molecular signatures of different tumor types and grades including brain, oral, lung, breast, gastric, pancreatic, renal, ovarian and prostate cancers (Groseclose, et al. 2008; Nathan, et al. 2002; Oppenheimer, et al. 2010 and Yanagisawa, et al. 2003).

SUMMARY OF THE INVENTION

Thus, in accordance with the present invention, there is provided a method of differentiating Spitz nevi from Spitzoid malignant melanoma comprising (a) subjecting a skin lesion sample from a patient to mass spectrometry; (b) obtaining a mass spectrometric protein profile from the sample; (c) comparing the mass spectrometric protein profile to a known normal, Spitz nevi and/or Spitzoid malignant melanoma profile; and (d) classifying the lesion as a Spitz nevi or Spitzoid malignant melanoma based on the similarities and differences between the mass spectrometric protein profile and the known profile or profiles.

The mass spectrometry may be secondary ion mass spectrometry, laser desorption mass spectrometry, matrix assisted laser desorption mass spectrometry, electrospray mass spectrometry, or desorption electrospray ionization. The method may further comprise obtaining the sample from the patient. The method may further comprise making a treatment decision for a patient from which the tissue was obtained. The patient may be identified as having Spitz nevi, and then the method may further comprise repeating steps (a)-(d) on the lesion in 6-12 months, 6-18 months, 6-24 months, 12-18 months, 12-24 months or 18-24 months. The patient may be identified as having Spitzoid malignant melanoma, then the method may further comprise treating the patient with chemotherapy, immunotherapy, toxin therapy or radiotherapy. The method may further comprise assessing one or more patient history parameters of the patient.

The method may further comprise performing a mass spectrometric analysis of a known Spitz nevi and/or Spitzoid malignant melanoma lesion. The method may further comprise performing histologic analysis on the skin lesion sample. The method may further comprise making a prediction of the patient's survival based on the classification.

The skin lesion sample may consist essentially of melanocytic components, and the mass spectrometric profile may comprise markers of vimentin and actin, or comprises peptide peaks at m/z 976.5±0.2, m/z 1060.2±0.2, m/z 1410.7±0.2, m/z 1336.7±0.2 and m/z 1428.8±0.2. The skin lesion sample may consist essentially of stromal components, and the mass spectrometric profile may comprise peptide peaks at m/z 713.2±0.2, m/z 1251.8±0.2, m/z 1287.7±0.2, m/z 1365.8±0.2, m/z 1428.8±0.2, m/z 1685.9±0.2, m/z 2519.3±0.2, m/z 2632.3±0.2, m/z 2773.3±0.2, m/z 3224.5±0.2, m/z 3287.1±0.2 and m/z 3411.8±0.2. Both melanocytic and stromal components of the skin lesion sample may be examined. The patient may have previously had immunohistochemical analysis of the lesion, such as previous immunohistochemical analysis indicating that the lesion was a Spitz nevus or a Spitzoid malignant melanoma. The method may further comprise immunohistochemical analysis on the skin lesion sample.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-F. Histological evaluation of Spitz lesions. FIGS. 1A-C. An example of a compound SN (case #1). FIG. 1A, Low-power view showing a symmetric, well-circumscribed, and wedge-shaped proliferation of melanocytes in the epidermis and in the dermis. FIG. 1B, There are large vertical nests of melanocytes with clefts between the nests and the surrounding hyperplastic epidermis. FIG. 1C, The melanocytes are large, slightly pleomorphic, with vesicular nuclei, prominent nucleoli, and abundant pale cytoplasm. FIGS. 1D-F, An example of an SMM (case #33): FIG. 1D, Asymmetric and poorly circumscribed proliferation of melanocytes in the epidermis and dermis. FIG. 1E, Large confluent nests of melanocytes, focally forming sheets in the dermis, and irregular nests and single melanocytes in the epidermis. FIG. 1F, Markedly pleomorphic melanocytes with vesicular nuclei, prominent nucleoli, eosinophilic cytoplasm, and numerous mitotic figures (arrows).

FIGS. 2A-G. A case of SMM (case #53) with circled foci marking the locations of the tumor (melanocytic) and dermal (TME) components to be studied by IMS. FIGS. 2A and 2B, Low-power views of an asymmetric melanocytic proliferation in the dermis. FIGS. 2C, 2E, and 2F, Densely cellular areas of tumor containing pure population of melanocytes without intervening epithelial component, vessels, and collagen are selected for IMS analysis and marked blue for tumor. FIG. 2D, Circled areas in the dermis representing TME to be studied by IMS. FIG. 2G, An entire section with multiple foci marked blue for tumor and yellow for dermis to be subjected to IMS analysis. Each dot is with a diameter of 300 μm.

FIG. 3A, Overlay of the average spectra for SN and SMM in the training set. Arrows A, B, C, D, and E mark the 5 peptides of interest discriminating between SN and SMM. FIG. 3B, Peak with m/z ratio=976.49 showing a higher intensity in SMM than in SN. This peak corresponds to actin. FIG. 3C, Tryptic peptide with m/z ratio=1060.18 shows a higher intensity in SN. FIG. 3D, Tryptic peptide with m/z ratio=1428.77 corresponding to vimentin.

FIGS. 4A and 4B, The peak corresponding to vimentin with m/z 1428.77. FIG. 4C, Example of an MS/MS spectrum acquired directly from the FFPE tissue section and sequenced as the tryptic peptide vimentin.

DESCRIPTION OF ILLUSTRATIVE EMBODIMENTS

Figure 3A:
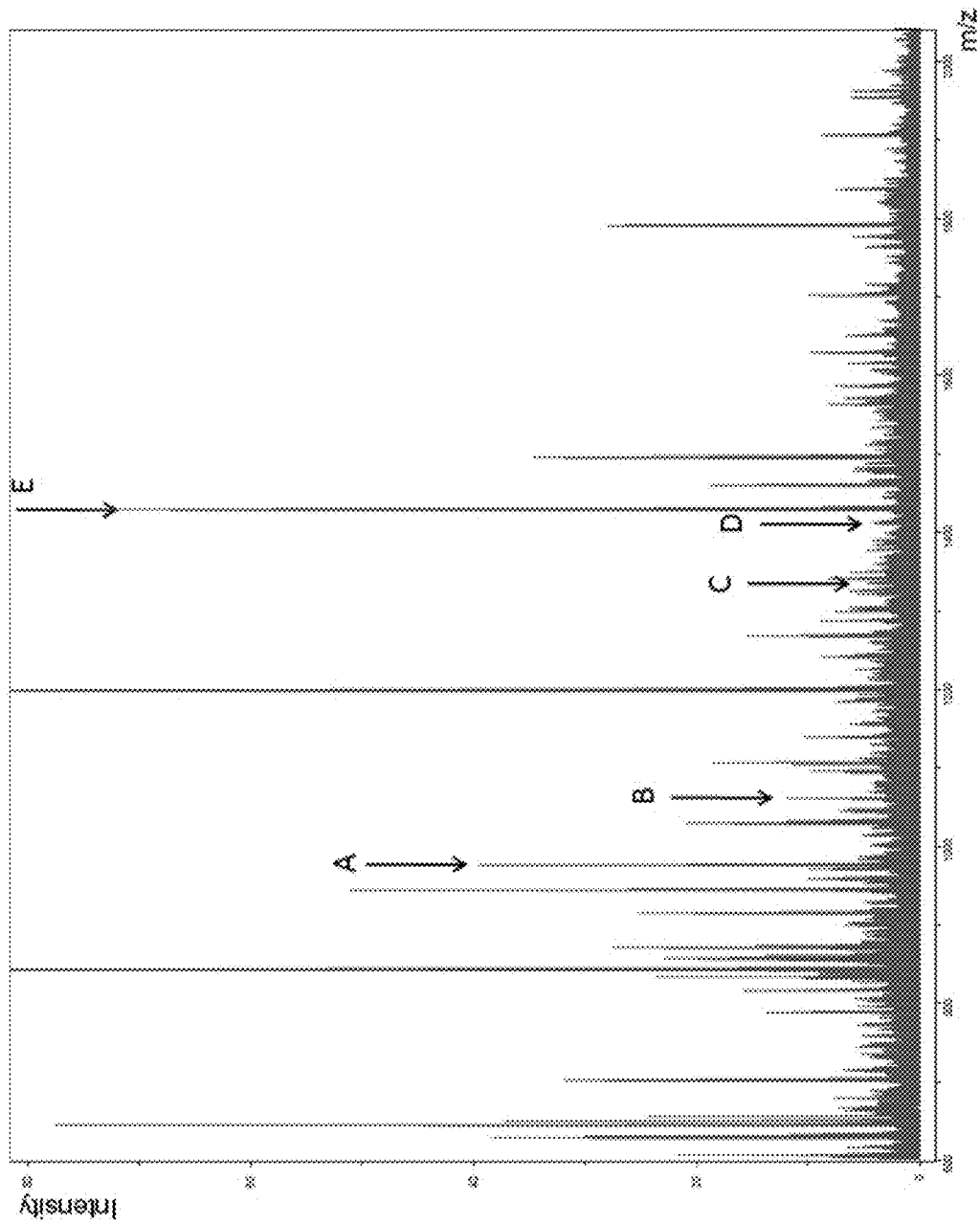
FIGS. 3A-D.
Figure 3B:
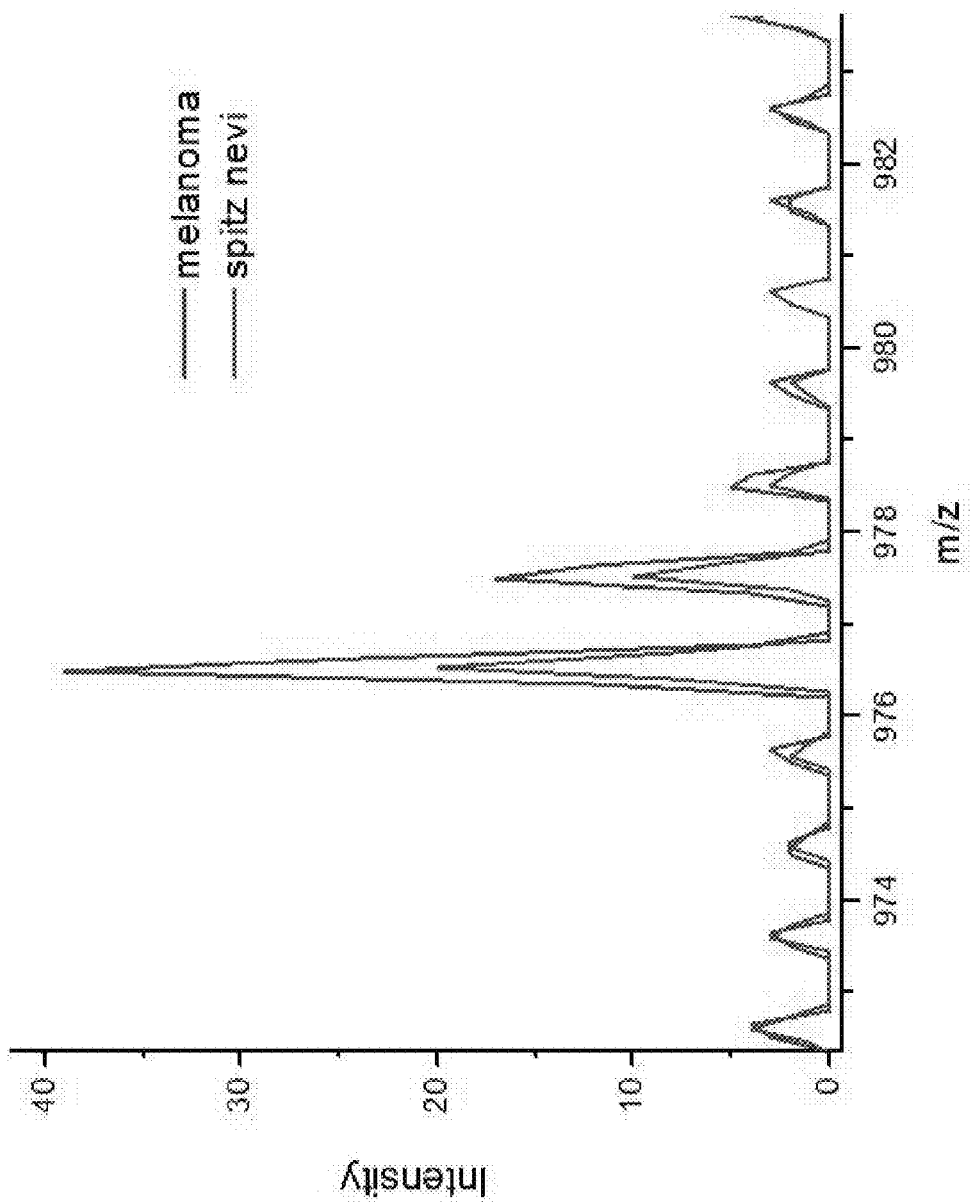
Figure 3C:
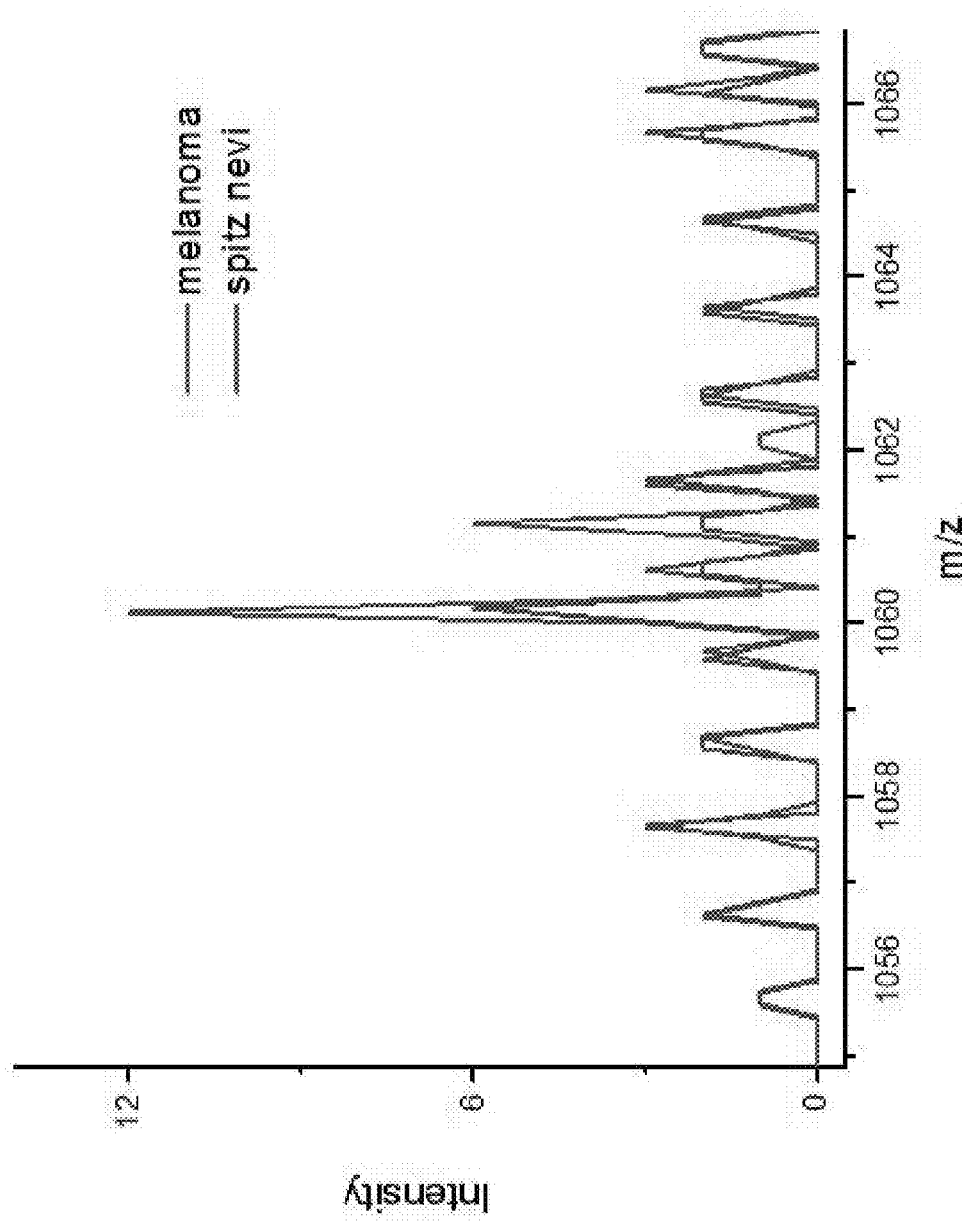
Figure 3D:
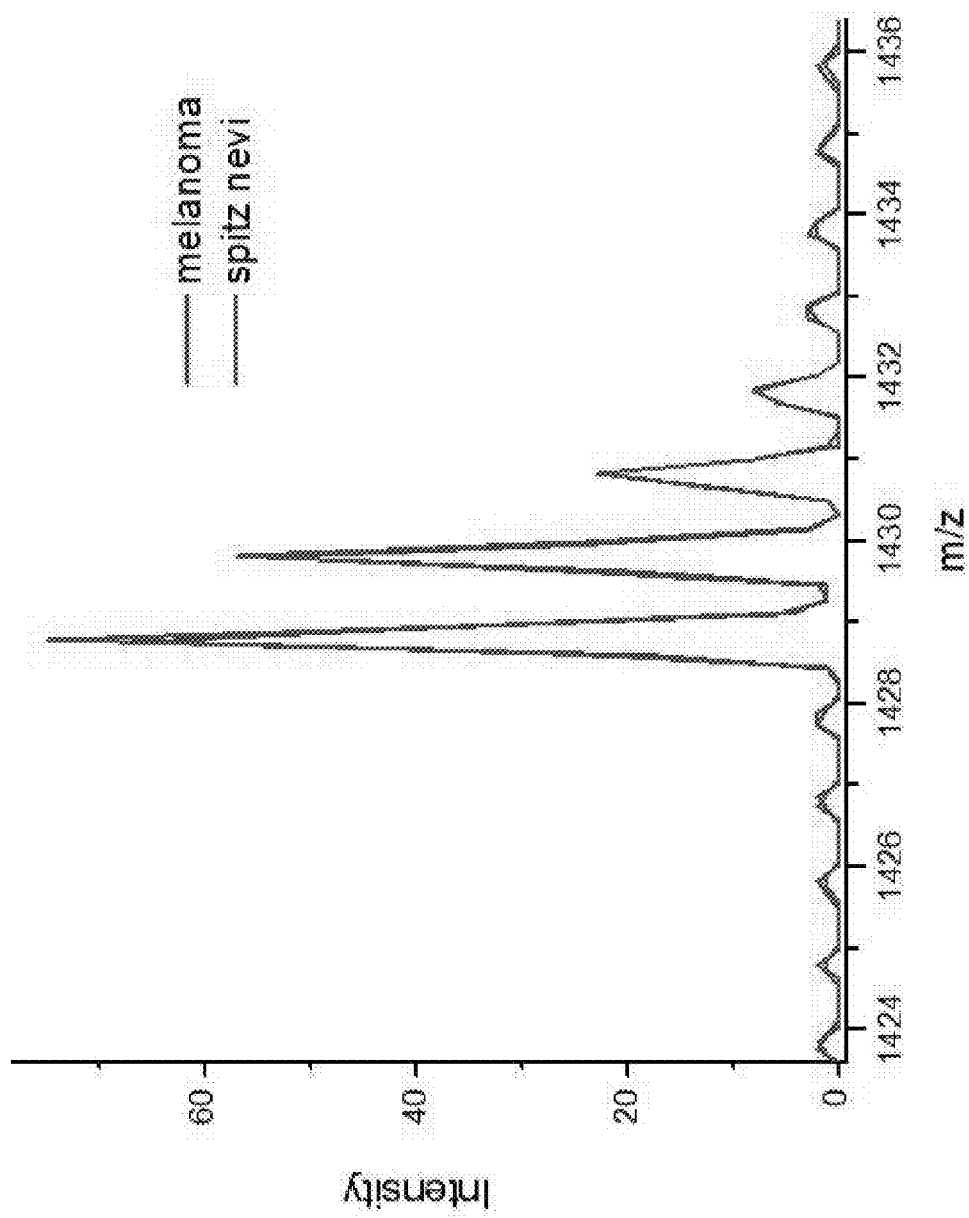

The presence of a gray area, in which it is extremely difficult or utterly impossible to distinguish between SN and SMM, prompted the work described here. Because both SN and SMM are composed of large epithelioid cells with abundant cytoplasm containing ample amount of proteins, the inventors hypothesized that there were proteomic differences, which might be able to differentiate between the two groups. They applied IMS to find specific proteomic markers to aid in the diagnosis of SN and SMM.

This study shows that SN and SMM can be successfully distinguished using MALDI IMS analysis based on detection of proteomic differences. MALDI IMS can profile tryptic peptides in FFPE sections and has been used to identify proteomic patterns to accurately diagnose and classify different tumor types and grades including brain, oral, lung, breast, gastric, pancreatic, renal, ovarian and prostate cancers (Groseclose, et al. 2008; Nathan, et al. 2002; Oppenheimer, et al. 2010 and Yanagisawa, et al. 2003). Behavior of genome products is difficult to predict from the gene sequence alone and measurement of gene expression at the protein level is more informative, because protein contains information that collectively indicates the actual rather than the potential functional state (Conrad, et al. 2008).

The inventors were able to differentiate SN from SMM with 97% sensitivity and 90% specificity in the validation cohort, when the discriminatory criteria obtained from the training cohort for tumor were used. The GA algorithm used in these experiments incorporated 5 peaks for the tumor, determined through statistical comparison of the peaks in the training sets for both SN and SMM. In addition to analysis of the tumor, a proteomic signature for TME in the dermis in cases of SN and SMM was developed. Interestingly, the method was able to classify correctly 28 of 31 SMM based on proteomic differences in the dermis alone. It is conceivable that growth factors, cytokines, and other components are being actively secreted in the immediate TME surrounding SMM, whereas they are not present in such quantities near SN. Using data from the TME may be helpful in correctly diagnosing cases with equivocal results based on tumor analysis.

Molecular imaging and signature identification by IMS allows one to look beyond classic histology. Statistical analysis of IMS data uses computer-generated statistical models in the construction of the algorithm and data are analyzed objectively. Proteomic signatures established using MS classification can be used as a supplement to standard histology. This successful use of FFPE tissue further supports the practicability of combining MS analysis with histopathology in evaluation of Spitzoid melanocytic lesions. MS analysis could be particularly useful in cases that are histologically equivocal, and a firm diagnosis of SN or SMM cannot be made with absolute certainty.

By exploring the Spitzoid lesions in the histologically equivocal area, for which clinical followup data are available, one can reclassify these lesions in either the benign or malignant category based on their proteomic signature and correlate the results with the clinical information, the goal being to more reliably differentiate between SN and SMM and significantly narrow the "gray zone" in which difficult Spitzoid melanocytic neoplasms with unknown biologic potential cannot be reliably diagnosed microscopically. Future studies would be necessary to confirm these findings with larger sample sets, thereby achieving improved statistical confidence.

This appears to be the first study employing IMS as a novel tool in the evaluation of SN and SMM. Based on these results, IMS is an excellent ancillary method to confirm the diagnosis of SN with 97% accuracy. These findings demonstrate that this technology may be a valuable adjunct to histopathologic evaluation of Spitzoid lesions. The identification of differences on a protein level within the melanocytes in SN and SMM provides a more objective method using molecular and biochemical protein biomarkers to aid in the diagnosis of these disease, especially in conjunction with conventional histopathologic examination. Furthermore, identification of protein expression profiles, which discriminate between SN and SMM, may provide specific tumor biomarkers that can be incorporated into standard diagnostic and treatment strategies.

I. Spitz Nevi

A Spitz nevus (also known as an "epithelioid and spindle-cell nevus," "benign juvenile melanoma" and "Spitz's juvenile melanoma") is a benign melanocytic nevus, a type of skin lesion, affecting the epidermis and dermis. Although they are most commonly found on people in their first two decades of life, the age range for people with Spitz nevi is from 6 months to 71 years, with a mean age of 22 years and a median age of 19 years.

Spitz nevi characteristically have vertically arranged nests of nevus cells that have both a spindled and an epithelioid morphology. Apoptotic cells may be seen at the dermoepidermal junction. The main histologic differential diagnoses are pigmented spindle cell nevus and malignant melanoma.

Spitz nevi are uncommon. Their annual incidence was estimated in a coastal population of sub-tropical Queensland to be 1.4 cases per 100,000 people. For comparison, the annual incidence of melanoma in the same population, which is high by world standards, is 25.4 cases per 100,000 people.

The cause of Spitz nevi is not yet known. There is an association with sunburn, but causation is not established. Genetic studies of Spitz nevi have shown that most cells have the normal number of chromosomes, however a minority (25%) of cells have been shown to contain extra copies of parts of some chromosomes, such as chromosome 11p.

II. Spitzoid Malignant Melanoma

Melanoma is a malignant tumor of melanocytes. Melanocytes produce the dark pigment, melanin, which is responsible for the color of skin. These cells predominantly occur in skin, but are also found in other parts of the body, including the bowel and the eye (see uveal melanoma).

Melanoma can originate in any part of the body that contains melanocytes. Melanoma is less common than other skin cancers. However, it is much more dangerous if it is not found early. It causes the majority (75%) of deaths related to skin cancer. Worldwide, doctors diagnose about 160,000 new cases of melanoma yearly. It is more common in women than in men. In women, the most common site is the legs and melanomas in men are most common on the back. It is particularly common among Caucasians, especially northwestern Europeans living in sunny climates. There are high rates of incidence in Oceania, Northern America, Europe, southern Africa, and Latin America, with a paradoxical decrease in southern Italy and Sicily. This ographic pattern reflects the primary cause, ultraviolet light (UV) exposure crossed with the amount of skin pigmentation in the population.

According to a WHO report, about 48,000 melanoma related deaths occur worldwide per year. The treatment includes surgical removal of the tumor. If melanoma is found early, while it is still small and thin, and if it is completely removed, then the chance of cure is high. The likelihood of the melanoma coming back or spreading depends on how deeply it has gone into the layers of the skin. For melanomas that come back or spread, treatments include chemo- and immunotherapy, or radiation therapy.

Melanoma with features of a Spitz nevus is known as a "Spitzoid malignant melanoma." This is a cutaneous condition characterized histologically with tissue similar to a spitz nevus and with overall symmetry and a dermal nodule of epithelioid melanocytes that do not mature with progressively deeper dermal extension.

III. Protein-Based Detection—Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for grading gliomas and predicting glioma patient survival, without regard for the identity of specific proteins. Alternatively, given the established links with calcyclin, calpactin I light chain, astrocytic phosphoprotein PEA-15 and tubulin-specific chaperone A, mass spectrometry may be used to look for the levels of these proteins particularly.

1. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

2. ESI/MS/MS

In ESI tandem mass spectrometry (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

3. SIMS

Secondary ion mass spectrometry, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analyzed by the mass spectrometer in this method.

4. LD-MS and LDLPMS

Laser desorption mass spectrometry (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectrometry). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and the separation of fragments is due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

5. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al, 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multicomponent quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

IV. Immunohistochemistry

Antibodies may be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Thin sections of tissue specimens are collected onto microscope slides. Samples that have been formalin-fixed and paraffin embedded must be subjected to deparaffinization and antigen retrieval protocols prior to incubation with an antibody against the target protein of interest. Deparaffinization is accomplished by incubating the slides in xylene to remove the paraffin followed by graded ethanol and water to rehydrate the sections. Antigen retrieval is carried out through incubating the sections in buffer such as tris or citrate with heat which may be introduced via a pressure cooker or a microwave. Sections can then be stained with antibodies using a direct or indirect method.

The direct method is a one-step staining method and involves a labeled antibody (e.g. FITC-conjugated antiserum) reacting directly with the antigen in tissue sections. While this technique utilizes only one antibody and therefore is simple and rapid, the sensitivity is lower due to little signal amplification, such as with indirect methods, and is less commonly used than indirect methods.

The indirect method involves an unlabeled primary antibody (first layer) that binds to the target antigen in the tissue and a labeled secondary antibody (second layer) that reacts with the primary antibody. As mentioned above, the secondary antibody must be raised against the IgG of the animal species in which the primary antibody has been raised. This method is more sensitive than direct detection strategies because of signal amplification due to the binding of several secondary antibodies to each primary antibody if the secondary antibody is conjugated to the fluorescent or enzyme reporter.

V. Mass Spectrometry Target Proteins

As discussed above, the present invention provides a protein-based classification of Spitz-like skin lesions. This classification is based on the identification of peaks for at least five peptides, the expression of which correlates with the various disease states. Using information derived from these five targets, one can differentiate Spitz nevi from Spitzoid malignant melanoma.

1. Mass Spectrometry Profile

In one embodiment, the invention examines mass spectrometry profiles of proteins from various regions of a skin lesion sample. The sample contains both melanocytic and stromal components, and one can examine either or both of these regions.

With regarding to the melanocytic elements of the lesion, the invention identifies peptide peaks at m/z 976.5±0.2, m/z 1060.2±0.2, m/z 1410.7±0.2, m/z 1336.7±0.2 and m/z 1428.8±0.2 as providing relevant information on the nature of the lesion.

When examining stromal components of the lesion, peptide peaks at m/z 713.2±0.2, m/z 1251.8±0.2, m/z 1287.7±0.2, m/z 1365.8±0.2, m/z 1428.8±0.2, m/z 1685.9±0.2, m/z 2519.3±0.2, m/z 2632.3±0.2, m/z 2773.3±0.2, m/z 3224.5±0.2, m/z 3287.1±0.2 and m/z 3411.8±0.2 are found to be relevant in distinguishing Spitz nevi from malignant melanoma.

2. Classification Model

Spectral classification is achieved using the ClinProTools statistics package supplied by Bruker Daltonics. Spectra are organized and grouped according to the patient sample from which they originate. All spectra belonging to the same diagnosis are loaded into the software as a class with 2 or more classes being loaded for one analysis. All spectra are subjected to preprocessing which includes baseline subtraction, noise level estimation, and normalization to total ion current. Peak boundaries for integration and analysis are manually determined by selection of the monoisotopic peak. The peak data are then used to create a classification model using a Genetic Algorithm. In this approach, a set of peaks are chosen and evaluated for their ability to classify spectra into their correct diagnosis. This set of peaks is then crossed with another set of peaks, similar to genetic reproduction and the offspring evaluated for their classification ability. Those sets that perform better than the parents are further crossed with other sets to determine the most optimal set of peaks while those that perform worse, are discarded. This crossing and evaluation are carried out over 50 generations to determine the best optimized set of peaks for diagnostic classification. The maximum number of peaks to be used is set to 15, but the software determines the optimal number to include in the model.

Once a model has been optimized, it is evaluated using a leave-20%-out crossvalidation approach. A subset of 20% of the data is randomly selected to be left out and the remaining 80% are used to build the classification model. The model is then applied to the 20% that were originally left out and the accuracy of the classification determined. This is carried out over 10 iterations with a different random 20% left out each time.

Once an optimized classification model has been established, it can be applied to new data in one of two ways, either in a validation mode or a classification mode. In the validation mode, data are organized and identified as to the group to which they belong. The software then classifies the data and evaluates the accuracy of the classification reporting percentages of spectra correctly classified. In the classification mode, the researcher and the software are blinded as to the diagnoses of the sample from which the data originated. The software classifies the data into the group that it best matches and reports a list of classification results for each spectrum. Someone with knowledge of the clinical diagnosis of the samples must then evaluate the classification results as compared to the known diagnosis.

3. Protein Targets

Vimentin. Vimentin is a type III intermediate filament (IF) protein that is expressed in mesenchymal cells. IF proteins are found in all metazoan cells as well as bacteria. IF, along with tubulin-based microtubules and actin-based microfilaments, comprise the cytoskeleton. All IF proteins are expressed in a highly developmentally-regulated fashion; vimentin is the major cytoskeletal component of mesenchymal cells. Because of this, vimentin is often used as a marker of mesenchymally-derived cells or cells undergoing an epithelial-to-mesenchymal transition (EMT) during both normal development and metastatic progression.

A vimentin monomer, like all other intermediate filaments, has a central α-helical domain, capped on each end by non-helical amino (head) and carboxyl (tail) domains. Two monomers are likely co-translationally expressed in a way that facilitates their formation of a coiled-coil dimer, which is the basic subunit of vimentin assembly.

The α-helical sequences contain a pattern of hydrophobic amino acids that contribute to forming a "hydrophobic seal" on the surface of the helix. In addition, there is a periodic distribution of acidic and basic amino acids that seems to play an important role in stabilizing coiled-coil dimers. The spacing of the charged residues is optimal for ionic salt bridges, which allows for the stabilization of the α-helix structure. While this type of stabilization is intuitive for intrachain interactions, rather than interchain interactions, scientists have proposed that perhaps the switch from intrachain salt bridges formed by acidic and basic residues to the interchain ionic associations contributes to the assembly of the filament. Vimentin plays a significant role in supporting and anchoring the position of the organelles in the cytosol. Vimentin is attached to the nucleus, endoplasmic reticulum, and mitochondria, either laterally or terminally.

The dynamic nature of vimentin is important when offering flexibility to the cell. Scientists found that vimentin provided cells with a resilience absent from the microtubule or actin filament networks, when under mechanical stress in vivo. Therefore, in general, it is accepted that vimentin is the cytoskeletal component responsible for maintaining cell integrity.

Results of a study involving transgenic mice that lacked vimentin showed that the mice were functionally normal. While the outcome might seem surprising, it is possible that the microtubule network may have compensated for the absence of the intermediate network. This strengthens the suggestion of intimate interactions between microtubules and vimentin. Moreover, when microtubule depolymerizers were present, vimentin reorganization occurred, once again implying a relationship between the two systems. In essence, vimentin is responsible for maintaining cell shape, integrity of the cytoplasm, and stabilizing cytoskeletal interactions.

Also, vimentin is found to control the transport of low-density lipoprotein, LDL, -derived cholesterol from a lysosome to the site of esterification. With the blocking of transport of LDL-derived cholesterol inside the cell, cells were found to store a much lower percentage of the lipoprotein than normal cells with vimentin. This dependence seems to be the first process of a biochemical function in any cell that depends on a cellular intermediate filament network. This type of dependence has ramifications on the adrenal cells, which rely on cholesteryl esters derived from LDL.

It has been used as a sarcoma tumor marker to identify mesenchyme. Vimentin methylation has been established as a biomarker of colon cancer—this marker is being utilized in the development of fecal tests for colon cancer. Statistically significant levels of vimentin methylation have also been observed in certain upper gastrointestinal pathologies such as Barrett's esophagus, esophageal adenocarcinoma, and intestinal type gastric cancer.

Vimentin has been shown to interact with UPP1, MYST2, Desmoplakin, Plectin, SPTAN1, MEN1, Protein kinase N1 and YWHAZ. The 3' UTR of vimentin mRNA has been found to bind a 46 kDa protein.

Actin. Actin is a globular, roughly 42-kDa multi-functional protein found in all eukaryotic cells (the only known exception being nematode sperm), where it may be present at concentrations of over 100 μM. It is also one of the most highly-conserved proteins, differing by no more than 20% in species as diverse as algae and humans. Actin is the monomeric subunit of two types of filaments in cells: microfilaments, one of the three major components of the cytoskeleton, and thin filaments, part of the contractile apparatus in muscle cells. Thus, actin participates in many important cellular processes, including muscle contraction, cell motility, cell division and cytokinesis, vesicle and organelle movement, cell signaling, and the establishment and maintenance of cell junctions and cell shape. Many of these processes are mediated by extensive and intimate interactions of actin with cellular membranes. In vertebrates, three main groups of actin isoforms, α, β, and γ have been identified. The α actins, found in muscle tissues, are a major constituent of the contractile apparatus. The β and γ actins coexist in most cell types as components of the cytoskeleton, and as mediators of internal cell motility.

Principal interactions of structural proteins are at cadherin-based adherens junctions. Actin filaments are linked to α-actinin and to the membrane through vinculin. The head domain of vinculin associates to E-cadherin via α-, β-, and γ-catenins. The tail domain of vinculin binds to membrane lipids and to actin filaments.

The protein actin is one of the most highly conserved throughout evolution because it interacts with a large number of other proteins, with 80.2% sequence conservation at the gene level between *Homo sapiens* and *Saccharomyces cerevisiae* (a species of yeast), and 95% conservation of the primary structure of the protein product.

Mammals have at least six actin isoforms coded by separate genes, which are divided into three classes (α, β and γ) according to their isoelectric points. In general, alpha actins are found in muscle (α-skeletal, α-aortic smooth, α-cardiac, and γ2-enteric smooth), whereas beta and gamma isoforms are prominent in nonmuscle cells (β- and γ1-cytoplasmic). Although the amino acid sequences and in vitro properties of the isoforms are highly similar, these isoforms cannot completely substitute for one another in vivo.

The typical actin gene has an approximately 100-nucleotide 5' UTR, a 1200-nucleotide translated region, and a 200-nucleotide 3' UTR. The majority of actin genes are interrupted by introns, with up to six introns in any of 19 well-characterised locations. The high conservation of the family makes actin the favoured model for studies comparing the introns-early and introns-late models of intron evolution.

All nonspherical prokaryotes appear to possess genes such as MreB, which encode homologues of actin; these genes are required for the cell's shape to be maintained. The plasmid-derived gene ParM encodes an actin-like protein whose polymerised form is dynamically unstable, and appears to partition the plasmid DNA into the daughter cells during cell division by a mechanism analogous to that employed by microtubules in eukaryotic mitosis. Actin is found in both smooth and rough endoplasmic reticulums.

Actin forms microfilaments which are typically one of the most dynamic of the three subclasses of the eukaryotic cytoskeleton.

In turn, this gives actin major functions in cells:
- to form microfilaments to give mechanical support to cells, and provide trafficking routes through the cytoplasm to support signal transduction
- to allow cell motility in cells which undergo amoeboid motion using pseudopods (see actoclampin molecular motors) and phagocytosis, for example of bacteria by macrophages
- in metazoan muscle cells, to be the scaffold on which myosin proteins generate force to support muscle contraction
- in nonmuscle cells, to be a track for cargo transport myosins (nonconventional myosins) such as myosin V and VI.

The polarity of an actin filament can be determined by decorating the microfilament with myosin "S1" fragments, creating barbed (+) and pointed (−) ends on the filament. An S1 fragment is composed of the head and neck domains of myosin II. Under physiologic conditions, G-actin (the monomer form) is transformed to F-actin (the polymer form) by ATP, where the role of ATP is essential.

Actin polymerization and depolymerization is necessary in chemotaxis and cytokinesis. Nucleating factors are necessary to stimulate actin polymerization. One such nucleating factor is the Arp2/3 complex, which mimics a G-actin dimer to stimulate the nucleation of G-actin (or monomeric actin). The Arp2/3 complex binds to actin filaments at 70 degrees to form new actin branches off of existing actin filaments. Also, actin filaments themselves bind ATP, and hydrolysis of this ATP stimulates destabilization of the polymer.

The growth of actin filaments can be regulated by thymosin and profilin. Thymosin binds to G-actin to buffer the polymerizing process, while profilin binds to G-actin to exchange ADP for ATP, promoting the monomeric addition to the barbed, plus end.

Individual subunits of microfilaments are known as globular actin (G-actin). G-actin subunits assemble into long filamentous polymers called F-actin. Two parallel F-actin strands must rotate 166 degrees to layer correctly on top of each other. This creates the double helix structure of the microfilaments of the cytoskeleton. Microfilaments measure approximately 7 nm in diameter with a loop of the helix repeating every 37 nm.

In muscle, actin is the major component of thin filaments, which, together with the motor protein myosin (which forms thick filaments), are arranged into actomyosin myofibrils. These fibrils comprise the mechanism of muscle contraction. Using the hydrolysis of ATP for energy, myosin heads undergo a cycle during which they attach to thin filaments, exert a tension, and then, depending on the load, perform a power stroke that causes the thin filaments to slide past, shortening the muscle.

In contractile bundles, the actin-bundling protein alpha-actinin separates each thin filament by ~35 nm. This increase in distance allows thick filaments to fit in between and interact, enabling deformation or contraction. In deformation, one end of myosin is bound to the plasma membrane, while the other end "walks" toward the plus end of the actin filament. This pulls the membrane into a different shape relative to the cell cortex. For contraction, the myosin molecule is usually bound to two separate filaments and both ends simultaneously "walk" toward their filament's plus end, sliding the actin filaments closer to each other. This results in the shortening, or contraction, of the actin bundle (but not the filament). This mechanism is responsible for muscle contraction and cytokinesis, the division of one cell into two.

Actin is essential for transcription from RNA polymerases I, II and III. In Pol I transcription, actin and myosin (MYO1C, which binds DNA) act as a molecular motor. For Pol II transcription, β-actin is needed for the formation of the preinitiation complex. Pol III contains β-actin as a subunit. Actin can also be a component of chromatin remodeling complexes as well as pre-mRNP particles (that is, precursor messenger RNA bundled in proteins), and is involved in nuclear export of RNAs and proteins.

VI. Spitzoid Malignant Melanoma Therapies

A. Spitz Nevi

The treatment for benign Spitz nevi is watchful waiting or excision of the nevus for histological evaluation. If the lesion is confirmed to be benign, no further treatment is needed. A malignant Spitzoid melanoma must be surgically removed with sufficient normal appearing margins as determined by the depth that the lesion penetrates into the skin and underlying tissue. For example, a lesion that is 1 mm in depth requires a margin of 1 cm of healthy tissue while a lesion of 2-4 mm in depth requires a margin of 2 cm. Patients that are determined to have malignant disease through histological evaluation are generally subjected to a sentinel lymph node biopsy for determination if the tumor has metastasized. Patients with metastatic disease are then treated with chemotherapy. As Spitzoid nevi commonly occur on the faces of young children, excessive surgical excision due to incorrect diagnosis and lymph node biopsy should obviously be avoided. Improved diagnosis through molecular markers can help to reduce unnecessary surgical excision and resulting disfigurement.

B. Spitzoid Malignant Melanoma

Given the aggressive nature of malignant melanomas, therapy is also aggressive and includes chemotherapy, immunotherapy, cytokine therapy and surgery, including combinations thereof (in particular chemo- and cytokine therapy).

Dacarbazine. Dacarbazine is an antineoplastic chemotherapy drug used in the treatment of various cancers, among them malignant melanoma, Hodgkin lymphoma, sarcoma, and islet cell carcinoma of the pancreas. Dacarbazine is a member of the class of alkylating agents, which destroy cancer cells by adding an alkyl group ($C_nH_{2n+1}$) to its DNA.

Dacarbazine is normally administered by intravenous infusion (IV) under the immediate supervision of a doctor or nurse. Dacarbazine is bioactivated in liver by demethylation to "MTIC" and then to diazomethane, which is an "alkylating agent."

Like many chemotherapy drugs, dacarbazine may have numerous serious side effects, because it interferes with normal cell growth as well as cancer cell growth. Among the most serious possible side effects are birth defects to children conceived or carried during treatment; sterility, possibly permanent; or immune suppression (reduced ability to fight infection or disease). Dacarbazine is considered to be highly emetogenic, and most patients will be pre-medicated with antiemetic drugs like palonosetron or aprepitant. Other significant side effects include headache, fatigue and occasionally diarrhea.

Interleukin-2 (IL-2). Interleukin 2 (IL-2) is an interleukin, a type of cytokine signaling molecule in the immune system. It is a protein that regulates the activities of white blood cells (leukocytes, often lymphocytes) that are responsible for immunity. IL-2 is part of the body's natural response to microbial infection, and in discriminating between foreign ("non-self") and "self." IL-2 mediates its effects by binding to IL-2 receptors, which are expressed by lymphocytes.

IL-2 is necessary for the growth, proliferation, and differentiation of T cells to become 'effector' T cells. IL-2 is normally produced by T cells during an immune response. Antigen binding to the T cell receptor (TCR) stimulates the secretion of IL-2, and the expression of IL-2 receptors IL-2R. The IL-2/IL-2R interaction then stimulates the growth, differentiation and survival of antigen-specific CD4+ T cells and CD8+ T cells. As such, IL-2 is necessary for the development of T cell immunologic memory, which depends upon the expansion of the number and function of antigen-selected T cell clones.

IL-2 is also necessary during T cell development in the thymus for the maturation of a subset of T cells that are termed regulatory T cells (T-regs). After exiting from the thymus, T-Regs function to prevent other T cells from recognizing and reacting against self antigens, which could result in autoimmunity. T-Regs do so by preventing the responding cells from producing IL-2. Also, because T-Reg cells constitutively express IL-2 receptors, they bind, internalize and degrade IL-2, thereby depriving neighboring effector T cells of IL-2. Thus, IL-2 is required to discriminate between self and non-self, one of the other hallmarks of the immune system.

IL-2 has been tested in many clinical trials as an immunotherapy for the treatment of cancers, chronic viral infections and as adjuvants for vaccines.

A recombinant form of human IL-2 for clinical use is manufactured by Prometheus Laboratories, Inc. with the brand name Proleukin. It has been approved by the Food and Drug Administration (FDA) for the treatment of cancers (malignant melanoma, renal cell cancer) in large intermittent toxic doses, and is in clinical trials for the treatment of chronic viral infections, and as a booster (adjuvant) for vaccines. The use of large, toxic doses of IL-2 given every 6-8 weeks in HIV therapy, similar to its use in cancer therapy, has been found recently to be ineffective in preventing progression to an AIDS diagnosis in two large clinical trials. However, that does not mean that the drug is ineffective in improving T-cell count. Many persons who underwent IL-2 therapy enjoyed dramatic improvement in T-cell count, as well as overall health. But the FDA determined that the risks and costs (experience of side-effects) outweighed those benefits. A recent study in which post-chemotherapy, stage 1V cancer patients were given a non-toxic, lower dose of IL-2 in combination with 13-cis retinoic acid showed remarkable improvement in five year survival rates.

Tremelimumab. Tremelimumab is a fully human IgG2 monoclonal antibody produced by Pfizer, undergoing human trials for the treatment of cancer.

Cytotoxic T lymphocytes (CTLs) can recognize and destroy cancer cells. However, there is also an inhibitory mechanism that interrupts this destruction. Tremelimumab turns off this inhibitory mechanism and allows CTLs to continue to destroy the cancer cells. Tremelimumab binds to the protein CTLA-4, which is expressed on the surface of activated T lymphocytes and inhibits the killing of cancer cells. Tremelimumab blocks the binding of the antigen-presenting cell ligands B7.1 and B7.2 to CTLA-4, resulting in inhibition of B7-CTLA-4-mediated downregulation of T-cell activation; subsequently, B7.1 or B7.2 may interact with another T-cell surface receptor protein, CD28, resulting in a B7-CD28-mediated T-cell activation unopposed by B7-CTLA-4-mediated inhibition. Tremelimumab stimulates patients' immune systems to attack their tumors. It has induced durable tumor responses in patients with metastatic melanoma in Phase 1 and Phase 2 clinical studies.

On Apr. 2, 2008, Pfizer announced that it has discontinued a Phase III clinical trial for patients with advanced melanoma after the review of interim data showed that the trial would not demonstrate superiority to standard chemotherapy. Studies for other tumors are planned as of October 2009, namely for prostate cancer and bladder cancer. On Oct. 4, 2011, MedImmune LLC gained worldwide rights on Tremelimumab to develop and commercialize the drug for treatment of cancer, while Pfizer retains all rights for combination therapies.

As of October 2009, there are two fully human anti CTLA-4 monoclonal antibodies in advanced clinical trials, tremelimumab and ipilimumab (from Medarex and Bristol-Myers Squibb).

Surgical Resection. One of the most effective surgical interventions for melanoma is Mohs surgery. In Mohs surgery, a microscope is used to trace the edges of these tumors and ensure the cancers are removed down to their roots during the initial surgery. Because of this microscopic precision, only the cancerous tissue is removed, while the surrounding healthy tissue is left intact and unharmed. It is for this reason that Mohs surgery is especially useful for anatomic and functionally important areas such as the eyelids, nose, and lips, as well as other cosmetically sensitive areas of the face.

Mohs surgery is also used to treat aggressive and/or recurrent skin cancers, skin cancers with ill-defined borders, cancers that arise in areas previously treated with radiation, and those patients with suppressed immune systems or specific genetic disorders. The Mohs technique is used most often to treat squamous and basal cell carcinomas. Some melanomas, as well as other types of skin cancer may be treated using Mohs.

Mohs surgery was initially developed by and named after Dr. Frederick Mohs, who worked at the University of Wisconsin. Today, Mohs surgery is performed by dermatologists who receive specialized training in the technique. The training programs are organized and directed by the American College of Mohs Surgeons in the United States. These comprehensive programs develop expertise in skin oncology, pathology and reconstructive surgery.

Tissue sparing and extraordinarily low recurrence rates make Mohs surgery the gold standard and procedure of choice for treating specific skin cancers. If you have been diagnosed with skin cancer, please contact the specialists at Sanova Dermatology to see if you would be a good candidate for Mohs surgery.

VII. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. In particular, intratumoral routes and sites local and regional to tumors are contemplated. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Tumor Specimens. The inventors collected archival formalin-fixed, paraffin-embedded (FFPE) tissue samples of SN and SMM from the Yale Spitzoid Neoplasm Repository. The Institutional Review Board at Yale University approved the study. The histopathology of each case was reviewed by the dermatopathologist to confirm the diagnosis. The study included histologically unequivocal SN and primary cutaneous SMM, which were diagnosed initially by a board-certified dermatopathologist. The majority of these cases were seen by multiple dermatopathologists at consensus conference at the time of the initial diagnosis. In addition, all cases chosen for the study underwent confirmatory review by at least 4 other dermatopathologists from Yale Dermatopathology Laboratory. Only cases with an unequivocal consensus diagnosis of SN or melanoma with Spitzoid features (SMM) were included in the study. Histologically ambiguous Spitzoid neoplasms or SN with atypical features were excluded from the study. The inventors selected SN and primary invasive SMM, which had an extensive and densely cellular dermal component with areas, in which tumors cells compiled almost pure populations of melanocytes, which allowed the collection of mostly melanocytes (>95%) for the analyzed samples. Included in the category of SN were melanocytic lesions, which qualified as SN based on diagnostic criteria that have been described previously (Paniago-Pereira et al., 1978 and Mones and Ackerman, 2003). Compound or predominantly intradermal SN with large nests and/or areas containing large groups of melanocytes without intervening dermis or epithelium were chosen. Excluded from the study were predominantly junctional SN and desmoplastic or purely intradermal SN. The study group of SMM consisted of malignant melanomas with Spitzoid features based on previously described criteria (Barnhill, et al. 1999; Paniago-Pereira et at., 1978; Reed 1999 and Spatz and Barnhill 1999). Invasive SMM with large nests of melanocytes and/or areas containing large groups of melanocytes without intervening dermis, epithelium, or inflammatory cells were included in the study. Excluded from the study were superficially invasive SMM with insufficient areas containing pure melanocytic population.

A total of 114 specimens, 56 SN and 58 SMM, were analyzed for tumor and tumor microenvironment (TME-dermis). The samples were randomly divided into 2 cohorts: a training set and a validation set. The training set consisted of 26 SN and 25 SMM. The validation set consisted of 30 SN and 33 SMM. Five of the 30 cases of SN in the validation set and 2 cases of SMM did not contain sufficient surrounding dermis for analysis. Furthermore, 4 cases of SMM from the validation set contained only dermis and had insufficient melanocytic component for analysis.

Mass Spectrometry Analysis. Serial sections, 5 mm thick, were cut from FFPE tissue blocks using a microtome. One section per sample was mounted onto a conductive glass slide, whereas the consecutive serial section was mounted onto a regular glass slide and stained with hematoxylin and eosin, which served as a reference section. Unstained sections were subjected to paraffin removal with xylene and graded ethanol washes. After air drying, antigen retrieval was performed by heating the sections in Tris buffer. Antigen-retrieved sections were stored in a desiccator at room temperature until matrix deposition for no longer than 2 days.

Mass spectral profiles were acquired in duplicates from the tissue using a histology-directed profiling approach as follows (Cornett, et al. 2006). Digital images were acquired of the histology slide using a Mirax Scan digital microscope slide scanner (Mirax, Budapest, Hungary) at a pixel resolution of 0.23 µm. The dermatopathologist (R.L.) marked 300-µm-diameter color-coded areas of interest (i.e., tumor and TME) on the digital image of the hematoxylin and eosin-stained section. The goal was to choose pure melanocytic populations for analysis of the tumor and without interference of other cell types such as endothelial cells from blood vessels, red blood cells, inflammatory cells, or epithelium. Samples from dermis in the area underlying the melanocytic lesion were also analyzed as TME.

Using image-processing software (Photoshop), the histology-marked image was merged to an image of the unstained section and the coordinates of annotations were determined. Using fiducial points visible in the image and on the MALDI target plate, an affine transform was used to transfer coordinates into an acoustic robotic microspotter (Labcyte, Sunnyvale, Calif.). A detailed description of the device and its operational conditions were described elsewhere (Aerni et al., 2006). The spotter is capable of depositing 170-pL-volume drops of matrix at very precise locations (spotting error <60 µm) at a rate of 30 Hz. On-tissue digestion was carried out by spotting trypsin solution onto the tissue section at the designated locations (spot diameter ~175 µm). Trypsin was spotted over a series of 40 iterations (1 drop each) with drying time (~2 minutes) between iterations. After trypsin deposition, matrix (10 mg/mL alpha-cyano-4-hyrdroxycinnamic acid in a mixture of 50:50:0.1 acetonitrile/$H_2O$/trifluoroacetic acid by volume) was spotted directly onto tryptic spots over 72 iterations (8 passes of 9 drops each). The spots were slightly smaller than the diameter of the annotations placed by the pathologist, allowing for slight placement error. Matrix spot placement accuracy was evaluated before coordinates were transferred to the mass spectrometer. Mass spectra were acquired in reflectron mode using an AutoFlex (Bruker Daltonics, Billerica, Mass.) equipped with a 355-nm Nd:YAG laser operating at a 1000-Hz repetition. Typically, 15-20 distinct spectra were collected from each tumor or TME area from each section. Peptide markers of interest were later identified directly from the unstained sections using MS/MS (tandem mass spectrometry) sequence analysis using an AutoFlex TOF/TOF (Bruker Daltonics). The tandem mass spectrometry (MS/MS) spectra were processed using FlexAnalysis. This included baseline correction, Savitzky-Golay smoothing, and monoisotopic peak picking. The spectra were submitted into a MASCOT (Matrix Science, Boston, Mass.) database search engine to match tryptic peptide sequences to their respective intact proteins. The tandem mass spectrometry spectrumsearch was performed with a peptide tolerance of 0.5 Da and a fragment tolerance of 0.5 Da. The search criteria also included one missed cleavage and variable modifications including lysine acetylation, N-terminus acetylation, C-terminus amidation, and methionine oxidation.

Data Analysis. Statistical analyses of MS profiles were carried out using ClinProTools 2.0 (Bruker Daltonics). Classes of spectra were loaded into the software, and baseline correction was achieved using a top hat algorithm with a 10% minimal baseline width. ClinProTools automatically normalizes all spectra to their own total ion current. Thus, for each spectrum, the total ion current is determined as the sum of intensities from all data points in the spectrum. Peaks in the spectra were selected manually, and the maximum intensity within each of the defined peak integration areas was used as the comparative value. The classification model used in this analysis was built in ClinProTools using a genetic algorithm (GA) (Holland, 1975) to determine the peak combination that separates best between SN and SMM. Maximum number of peaks was set to 15, maximum number of generations was 50, mutation rate was 0.2, and crossover rate was 0.5. The number of neighbors for the k nearest neighbors classification parameter in the GA settings was set to 3.

For the differentially expressed features identified in the 2 comparisons of tumor in SN versus tumor in SMM and TME in SN versus TME in SMM, a GA classifier was used to assess class prediction. The prediction accuracy was estimated using a leave-N-out-crossvalidation algorithm in which 20% of the data were randomly left out in each of 10 iterations (Harrell 2001). The classification model for SN and SMM were built using the GA, which then classified spectra in the validation cohort based on the supervised learning from the training set.

Example 2

Results

Characterization of the Study Sample. The cohort of SN came from patients, who ranged from 1 to 48 years of age (mean, 13; SD, 10.2), 30 male and 25 female patients. The lesions were distributed on the head and neck (17), leg (14), back (10), arm (9), buttock (2), abdomen (2), and chest (1). None of the lesions recurred or metastasized, and all patients are alive with a follow-up ranging from 2 to 20 years (mean, 10.7). The SMM cohort comprised patients from 29 to 89 years old (mean, 62; SD, 14), 32 male and 26 female patients. The distribution was as follows: leg (23), back (13), arm (12), scalp (4), chest (2), ear (2), and face (2). The depth of the SMM ranged from 0.75 to 9.0 mm (mean, 3.2 mm). The follow-up ranged from 1 to 21 years (mean, 5). Representative histopathologic features of 1 patient with SN (case #1) and 1 with SMM (case #33) are illustrated in FIGS. 1A-F. A summary of clinical and histopathologic characteristics of patients with SMM is shown in Table 1.

TABLE 1

Histopathological and Clinical Characteristics of Spitzoid Malignant Melanoma Cases

| Case No. | Age | Gender | Site | Depth (mm) | Clark Level | Ulceration/ Regression | Mitoses/ $mm^2$ | Follow-up (Years) | Adverse Event(s) | MS Results (Tumor) |
|---|---|---|---|---|---|---|---|---|---|---|
| 1 | 72 | F | Leg, lower | 4 | IV | No/Yes | <1 | 1 | DOD; satellitosis, 0/1 SLN | NA |
| 2 | 75 | M | Arm, upper | 1.3 | IV | No/Yes | 2 | 5 | Alive-NED; 0/5 SLN | NA |
| 3 | 54 | M | Back | 1.2 | IV | No/Yes | 2 | 5 | Alive-NED; 0/6 SLN | NA |
| 4 | 64 | F | Knee | 3.8 | IV | No/No | <1 | 3 | Alive-NED; 0/3 SLN | NA |
| 5 | 52 | F | Leg | 1.2 | IV | No/No | 2 | 5 | Alive-NFA | NA |
| 6 | 78 | F | Back | 3.5 | IV | Yes/No | 17 | 4 | Alive-NED | NA |
| 7 | 74 | M | Back | 3 | IV | Yes/No | 6 | 4 | Alive-NED; 0/1 SLN | NA |
| 8 | 48 | F | Leg, lower | 1.3 | IV | No/No | 1 | 4 | Alive-NED; 0/2 SLN | NA |
| 9 | 38 | F | Thigh | 1.9 | IV | Yes/No | 26 | 3 | Alive-NED; 1/2 SLN; 0/8 CLD | NA |
| 10 | 72 | M | Arm | 5.5 | IV | No/no | 5 | 3 | Alive w/d; multiple brain mets; 0/1 SLN | NA |
| 11 | 76 | F | Leg | 3.1 | IV | Yes/No | 2 | 3 | Alive-NED; 0/2 SLN | NA |
| 12 | 86 | M | Chest | 4.8 | IV | Yes/No | 2 | 3 | Alive-NED; 0/6 SLN | NA |
| 13 | 60 | M | Arm | 5 | IV | No/No | 4 | 2 | Alive w/d; multiple liver, brain, lung mets; 0/19 CLD | NA |
| 14 | 67 | M | Leg | 8 | V | Yes/No | 8 | 1 | DOD; brain and lung mets | NA |
| 15 | 56 | M | Ear | 2.3 | IV | No/No | 2 | 2 | Alive-NED; 0/3 SLN | NA |
| 16 | 88 | F | Leg | 2.5 | IV | No/No | 3 | 4 | NFA | NA |
| 17 | 78 | F | Scalp | 2.9 | IV | No/No | 5 | 2 | Alive-NED; 0/4 SLN | NA |
| 18 | 70 | M | Back | 3.4 | IV | No/No | 2 | 3 | Alive-NED; 1/4 SLN; 0/37 CLD | NA |
| 19 | 50 | M | Back | 3.2 | IV | No/No | 12 | 2 | Alive-NED; 0/2 SLN | NA |
| 20 | 57 | M | Arm | 3.4 | IV | No/No | 3 | 2 | Alive-NED; 0/2 SLN | NA |
| 21 | 53 | M | Leg | 1.9 | IV | No/No | 8 | 2 | Alive-NED; 0/2 SLN | NA |
| 22 | 62 | M | Leg, lower | 2.3 | IV | No/No | 2 | 2 | Alive-NED; 0/3 SLN | NA |
| 23 | 58 | M | Thigh | 2.1 | IV | No/No | 3 | 2 | Alive-NED; 1/3 SLN; 0/11 CLD | NA |
| 24 | 45 | F | Back | 2 | IV | No/No | <1 | 2 | Alive-NED; 1/6 SLN; 0/14 CLD | NA |
| 25 | 88 | M | Ear | 3 | IV | No/No | 2 | 2 | Alive-NED | NA |
| 26 | 64 | M | Leg | 7.5 | IV | No/No | 2 | 1 | Alive-NED; 1/4 SLN | + |
| 27 | 43 | M | Temple | 3.8 | IV | Yes/No | 10 | 14 | Alive-NED; 0/2 SLN; 1/29 CLD | + |
| 28 | 60 | M | Arm | 3.5 | IV | No/No | <1 | 4 | Alive-NED; 0/1 SLN | + |
| 29 | 44 | F | Leg | 0.75 | IV | No/No | 1 | 3 | Alive-NFA | + |
| 30 | 52 | F | Arm | 2.2 | IV | Yes/No | 4 | 3 | Alive-NED | + |
| 31 | 65 | F | Back | 1.1 | IV | No/No | <1 | 2 | Alive-NED | + |
| 32 | 51 | F | Leg | 0.9 | IV | No/No | <1 | 2 | Alive-NED; 0/4 SLN | + |
| 33 | 89 | F | Arm | 3 | IV | No/No | 4 | 2 | NFA | + |
| 34 | 58 | M | Back | 1.1 | III | No/No | 5 | 2 | Alive-NED; 0/2 SLN | + |
| 35 | 57 | F | Arm | 0.95 | IV | Yes/Yes | 2 | 4 | Alive-NED; 0/2 SLN | + |
| 36 | 46 | F | Arm | 1.3 | IV | No/No | 2 | 3 | Alive-NED | + |
| 37 | 52 | F | Abdomen | 13 | IV | Yes/No | 6 | 2 | Alive w/d; local recurrence, multiple brain and subcutaneous mets; 0/6 SLN; 1/19 CLD | + |
| 38 | 75 | M | Scalp | 2.1 | IV | No/No | 2 | 3 | DOD; satellitosis, multiple mets; 0/1 SLN | + |
| 39 | 59 | M | Leg | 2 | IV | No/No | <1 | 7 | Alive-NED; 0/7 SLN | + |
| 40 | 62 | M | Arm | 4.5 | IV | No/No | <1 | 7 | Alive-NED; 1/4 SLN and 0/5 CLD | + |
| 41 | 86 | M | Leg, lower | 5 | IV | No/No | 4 | 4 | DOD; local recurrence and multiple mets | + |
| 42 | 58 | F | Knee | 6 | IV | Yes/No | 6 | 2 | Alive-NED | + |
| 43 | 29 | M | Back | 2.5 | IV | Yes/No | 2 | 1 | Alive-NED; 0/2 SLN; 5/10 CLD | + |
| 44 | 50 | F | Thigh | 4.8 | IV | No/No | <1 | 1 | Alive-NED; 1/3 SLN; 0/4 CLD | |

TABLE 1-continued

Histopathological and Clinical Characteristics of Spitzoid Malignant Melanoma Cases

| Case No. | Age | Gender | Site | Depth (mm) | Clark Level | Ulceration/ Regression | Mitoses/ mm$^2$ | Follow-up (Years) | Adverse Event(s) | MS Results (Tumor) |
|---|---|---|---|---|---|---|---|---|---|---|
| 45 | 76 | M | Back | 2.1 | IV | Yes/No | 6 | 1 | Alive-NED; 0/4 SLN | + |
| 46 | 57 | M | Back | 4.8 | IV | Yes/No | 10 | 1 | NFA | + |
| 47 | 87 | F | Arm | 2.3 | IV | Yes/No | 18 | 1 | NFA | + |
| 48 | 38 | M | Chest | 8 | IV | Yes/No | 1 | 21 | Alive; R axilla 1/18 CLD; L axilla 4/15 CLD | + |
| 49 | 61 | M | Leg, lower | 2 | IV | Yes/No | 5 | 20 | Alive w/d; satellitosis, multiple mets; 2/25 CLD | |
| 50 | 75 | M | Scalp | 2.1 | IV | No/Yes | <1 | 3 | DOD; satellitosis, local recurrence, multiple mets | |
| 51 | 59 | M | Back | 2.9 | IV | No/No | <1 | 14 | Alive w/d; soft tissue mets; 0/12 CLD | + |
| 52 | 79 | F | Cheek | 9 | V | Yes/No | 2 | 2 | Alive-NFA | + |
| 53 | 69 | M | Back | 1.8 | IV | No/No | 17 | 2 | Alive-NED; 1/2 SLN in R axilla; 3/10 SLN in L axilla; 0/19 CLD | + |
| 54 | 51 | M | Knee | 1 | III | No/No | <1 | 2 | Alive-NFA | + |
| 55 | 53 | F | Leg | 1 | IV | No/No | 1 | 2 | Alive-NED; 0/2 SLN | ++ |
| 56 | 48 | F | Thigh | 0.8 | III | Yes/No | <1 | 8 | DOD; multiple mets | ++ |
| 57 | 62 | F | Scalp | 3.5 | IV | No/No | <1 | 2 | DOD; multiple mets; 1/11 CLD | ++ |
| 58 | 63 | F | Leg | 5.5 | IV | Yes/No | 5 | 2 | Alive-NED; 0/3 SLN | ++ |

Cases 1-25 are part of the teaching set and cases 26-58 are part of the validation set.
DOD, died of disease;
NED, no evidence of disease;
SLN, sentinel lymph node(s);
CLD, completion lymph adenectomy;
mets, metastases;
NA, not applicable;
NFA - no follow up available;
w/d, with disease;
LN, lymph nodes;
++, correct recognition based on dermis only (no tumor available).

Mass Spectrometry Analysis. Mass spectra from each dotted area (FIGS. 2A-G) on each sample from the training set were obtained in duplicates. Data were analyzed using GA, as described above, and classification models were built using a training set of biopsies from 26 SN and 25 SMM separately for tumor and for TME. Each peak in the mass spectra corresponds to a peptide at a specific m/z ratio. The spectra generated at each spot on the digested tissue typically contain many hundreds of distinct peaks with an signal-to-noise ratio>3. For the areas containing tumor, 5 peaks with the following m/z ratios, which were able to best discriminate between SN and SMM, were identified: 976.49, 1060.18, 1336.72, 1410.74, and 1428.77 (FIGS. 3A-D). Twelve peaks were found discriminatory and were used to build a classification model for the TME. Their m/z values were 713.19, 1251.75, 1287.70, 1365.81, 1428.81, 1685.92, 2519.26, 2632.31, 2773.26, 3224.46, 3287.51, and 3411.84.

The GA model was run against all spectra in the data set, and a summary table of the results was generated. The number of spectra in favor of SN and the number of spectra in favor of SMM were calculated. If the proportion of all spectra in favor of SN was higher, the case was classified as SN. Otherwise, it was classified as SMM.

After a molecular signature for both tumor and dermis was determined based on data from the training set, it was then tested on a validation cohort of 30 SN (30 cases with tumor, of which 25 also contained sufficient amount of dermis for analysis) and 33 SMM (29 cases with tumor of which 2 did not have sufficient amount of dermis, and 4 additional cases containing only dermis and not enough tumor component). The method was able to correctly recognize 29 of 30 SN (97%) in the validation cohort. There was only one SN, which was incorrectly classified. In this particular case, only 6 spectra were obtained due to very little tissue left in the block, whereas in the remaining cases of SN, the average number of tumor spectra obtained was 16. If this case were excluded from the analysis, the recognition would be 100% for SN. Twenty-six of 29 SMM (90%) were also recognized correctly based on tumor proteomic differences. Thus, this algorithm showed a sensitivity of 97% and specificity of 90% in correctly identifying SN based on tumor analysis in the validation set.

The dermis in 25 cases from SN and 31 cases of SMM was analyzed using the algorithm developed from the training set based on samples from TME. Twelve peptides within the TME of SN and SMM showed differences in their expression. The method correctly classified 28 of 31 (90%) SMM and 16 of 25 SN (64%) and showed a sensitivity of 64% and specificity of 90% for TME in identifying SN.

Figure 4A:
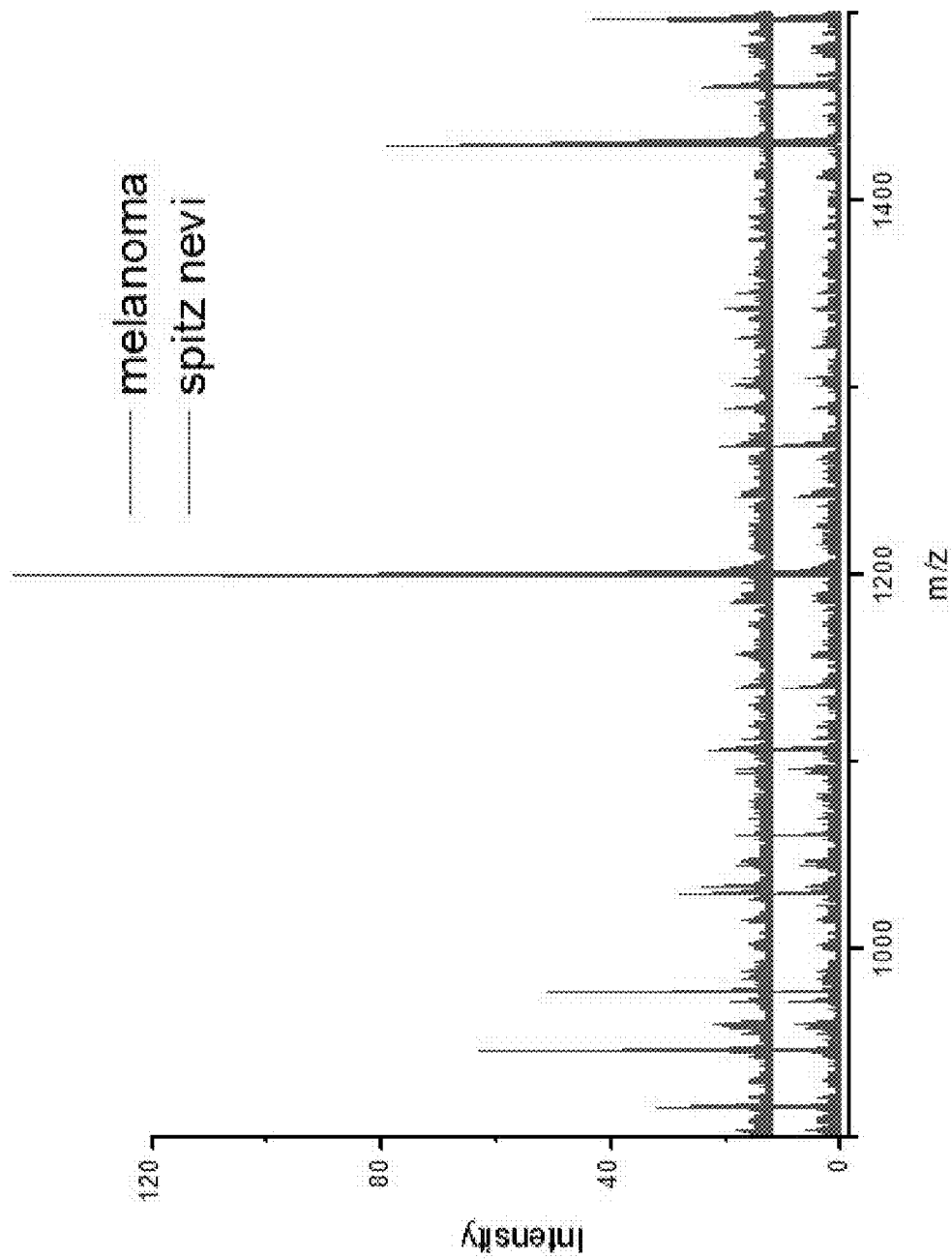
FIGS. 4A-C.
Figure 4B:
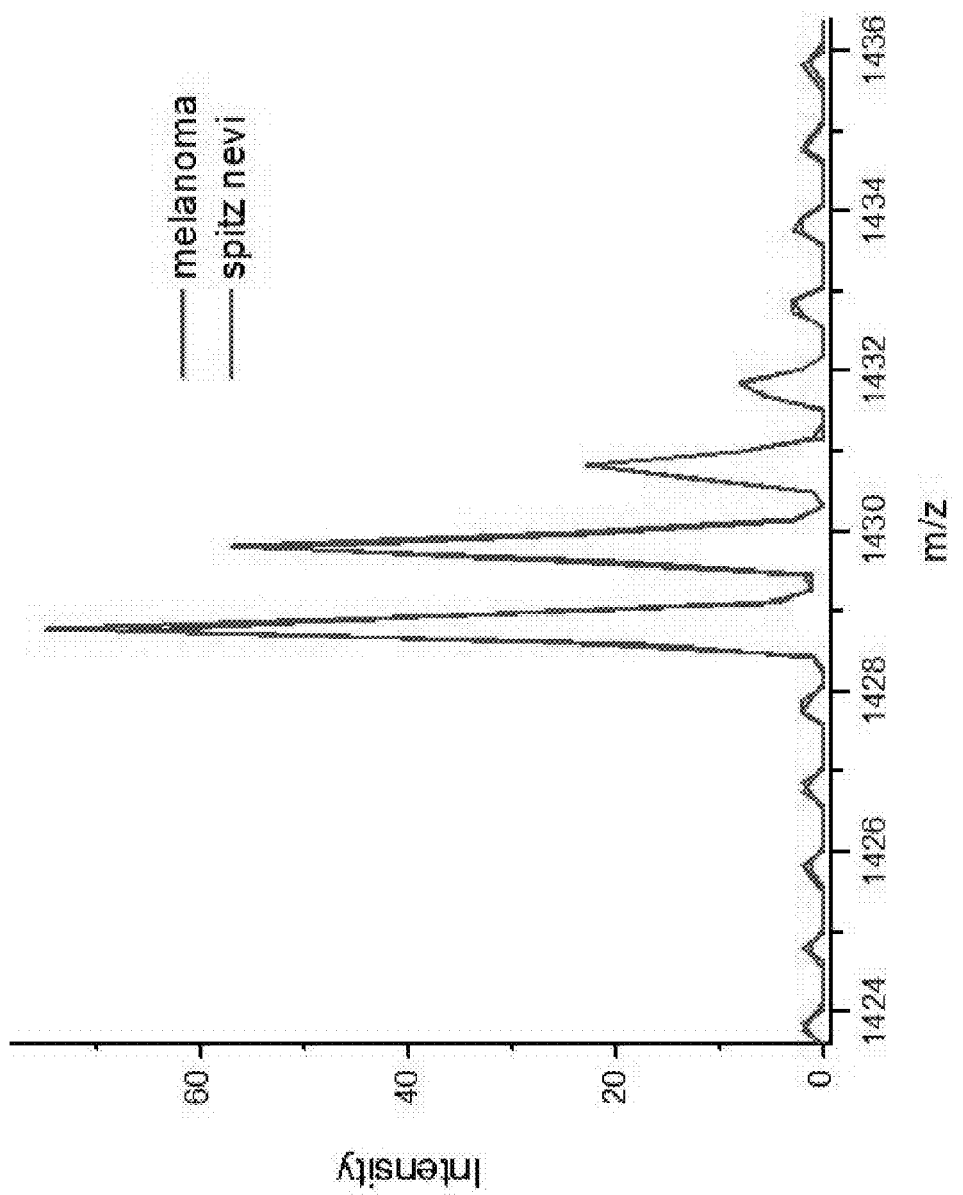
Figure 4C:
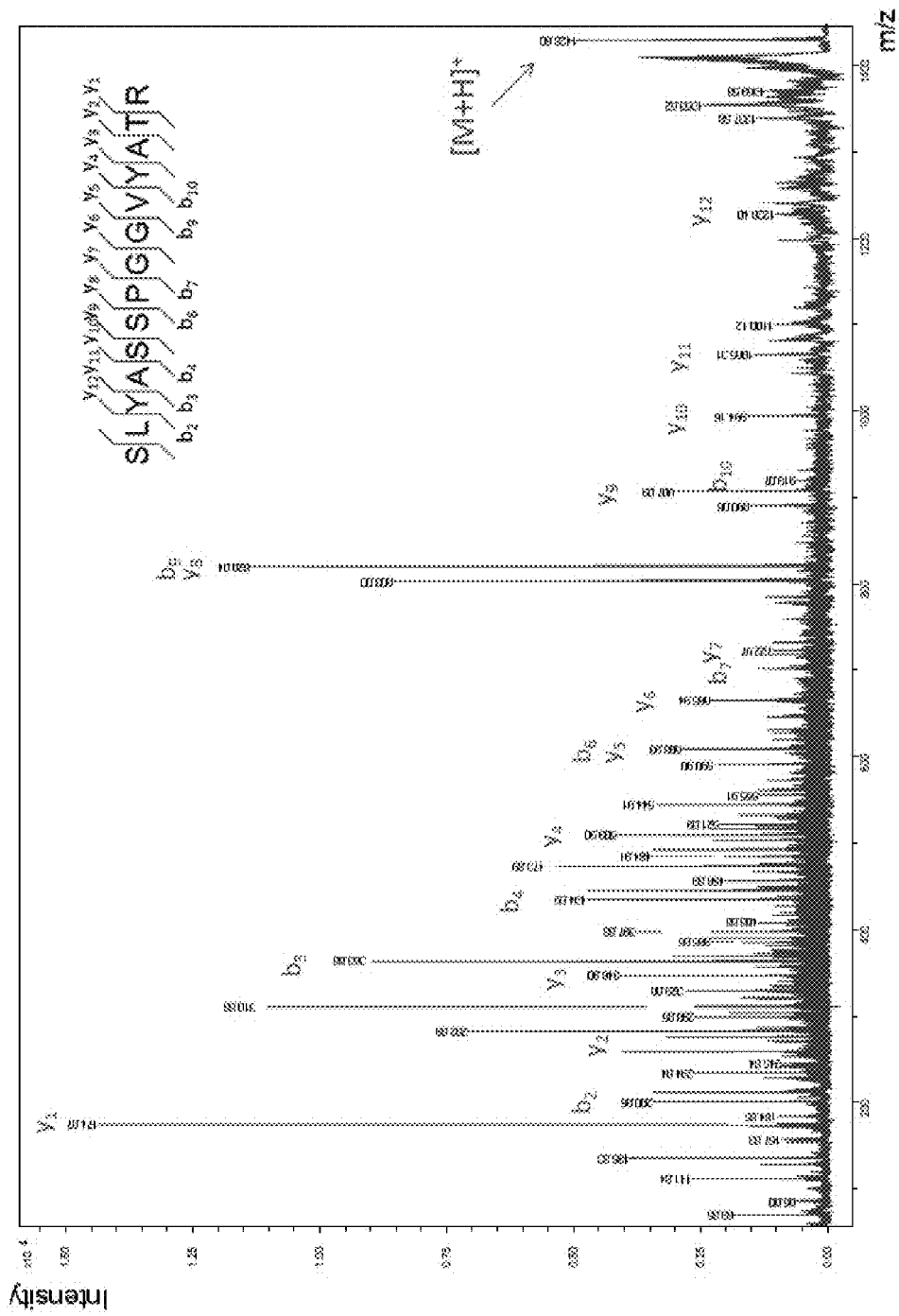

Protein Identification. The inventors identified two of the proteins differentially expressed by melanocytes in SN and SMM as actin (m/z=976.49) and vimentin (m/z=1428.61). Vimentin was identified against MASCOT database search with a probability-based Mowse score of 108 and a P value of $1.1 \times 10^8$ (FIGS. 4A-C).

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference.

U.S. Pat. No. 5,757,994
U.S. Pat. No. 5,788,166
U.S. Pat. No. 5,838,002
U.S. Pat. No. 5,849,486
U.S. Pat. No. 5,863,753
U.S. Pat. No. 5,916,779
U.S. Pat. No. 5,986,258
U.S. Pat. RE 35,413
Abbondanzo, *Ann Diagn Pathol*, 3(5):318-327, 1999.
Ackerman, *Hum Pathol.*, 27:1115-1116, 1996.
Allred et al., *Arch Surg*, 125(1):107-13, 1990.
Almendro et al., *J Immunol.*, 157:5411-5421, 1996.
Angel et al., *Mol. Cell. Biol.*, 7:2256, 1987a.
Aerni et al., Anal Chem., 78: 827-834, 2006.
Bahr et al., *J. Mass Spectrom.*, 32:1111-1116, 1997.
Barnhill et al., Hum Pathol., 30:513-520, 1990.
Barnhill et al., Cancer., 76:1833-1845, 1995.
Bastian et al., Cancer Res., 58:2170-2175, 1998.
Bastian et al., J Invest Dermatol., 113:1065-1069, 1999.
Bastian, Am J Pathol., 157:967-972, 2000.
Bastian et al., Am J Pathol., 163:1765-1770, 2003.
Bentzley et al., *Anal Chem.*, 68(13):2141-2146, 1996.
Binder et al., Semin Diagn Pathol., 10:36-46. 1993.
Brown et al., *Immunol Ser*, 53:69-82, 1990.
Bucknall et al., *J. Am. Soc. Mass Spectrom.*, 13(9):1015-1027, 2002.
Caprioli et al., *Anal Chem.*, 69:4751-4760, 1997.
Carbonelli et al., *FEMS Microbiol Lett*, 177(1):75-82, 1999.
Castillo et al., *Neuroepidemiology*, 23:85-93, 2004.
Chaurand et al., *Anal Chem.*, 71(23):5263-5270, 1999.
Chen et al., *Nat. Biotechnol.*, 19:537-542, 2001.
Conrad et al., J Intern Med., 23(suppl 1): 78-84, 2008.
Cornett et al., Mol Cell Proteomics., 5: 1975-1983, 2006.
Crotty et al., Pathology., 34: 6-12, 2002.
Curtin et al., N Engl J. Med., 353:2135-2147, 2005.
Desiderio et al., *J. Mass Spectrom.*, 35(6):725-733, 2000.
Desiderio et al., *Methods Mol. Biol.*, 61:57-65, 1996.
Duncan et al., *Rapid Commun. Mass Spectrom.*, 7(12):1090-1094, 1993.
Farmer, Hum Pathol., 27:528-531, 1996.
Faulstich et al., *Anal. Chem.*, 69(21):4349-4353, 1997.
Fenn et al., *Science*, 246(4926):64-71, 1989.
Ferrara et al., Arch Dermatol., 141:1381-1387, 2005.
Firak and Subramanian, *Mol. Cell. Biol.*, 6:3667, 1986.
Fullen et al., Mod Pathol., 19:1324-1332, 2006.
Gaiser et al., Mod Pathol., 23:413-419, 2010.
Gill et al., Cancer., 101:2636-2640, 2004.
Gloss et al., *EMBO J.*, 6:3735, 1987.
Gobom et al., *Anal. Chem.*, 72(14):3320-3326, 2000.
Groseclose et al., Proteomics., 8: 3715-3724, 2008.
Harland and Weintraub, *J. Cell Biol.*, 101:1094-1099, 1985.
Harrell, Regression Modeling Strategies. New York, N.Y.: Springer; 2001.
Harvell et al., Diagn Mol. Pathol., 13:22-25, 2004.
Haslinger and Karin, *Proc. Natl. Acad. Sci. USA*, 82:8572, 1985.
Holland, J. Adaptation in Natural and Artificial Systems. Ann Arbor, Mich.: University of Michigan Press; 1975.
Horak et al., *Rapid Commun. Mass Spectrom.*, 15(4):241-248, 2001.
Horwich et al., *Virol.*, 64:642-650, 1990.
Jespersen et al., *Anal Chem.*, 71(3):660-666, 1999.
Jiang et al., *J. Agric. Food Chem.*, 48:3305, 2000.
Kabarle et al., *Anal. Chem.* 65(20):972A-986A, 1993.
Kanazawa et al., *Biol. Pharm. Bull.*, 22(4):339-346, 1999.
Karin et al., *Mol. Cell. Biol.*, 7:606, 1987.
Kazmaier et al., *Anesthesiology*, 89(4):831-817, 1998.
Lebkowski et al., *Mol. Cell. Biol.*, 8(10):3988-3996, 1988.
Lee et al., Cancer, 106: 907-913, 2006.
Mones, Am J Dermatopathol., 25:223-238, 2003.
Nathan et al., Laryngoscope., 112:2129-2140, 2002.
Nelson et al., *Anal. Chem.*, 66:1408, 1994.
Oppenheimer et al., J Proteome Res., 9:2182-2190, 2010.
Paniago-Pereira, Arch Dermatol., 114:1811-1823, 1978.
Rapini, Semin Cutan Med. Surg., 18: 56-63, 1999.
Raskin et al., Am J Surg Pathol., 35:243-252, 2011.
Reed, Hum Pathol., 30:1523-1526, 1999.
Roepstorff, *EXS.*, 88:81-97, 2000.
Spatz and Barnhill, J Am Acad Dermatol., 40:223-228, 1999.
Stoeckli et al., *Nat. Med.*, 7(4):493-496, 2001.
Takach et al., *J. Protein Chem.*, 16:363, 1997.
van Engen-van Grunsven A C et al., *Am J Surg Pathol.*, 34:1436-1441, 2010.
Villanueva et al., *Enzyme Microb. Technol.*, 29:99, 1999.
Wang et al., *Anal. Chem.*, 72(21):5285-5289, 2000.
Wang et al., *J. Agric. Food. Chem.*, 47:1549, 1999.
Wang et al., *J. Agric. Food. Chem.*, 47:2009, 1999.
Wittmann et al., *Biotechnol. Bioeng.*, 72:642, 2001.
Wong et al., *Gene*, 10:87-94, 1980.
Wu et al., *Anal. Chem.*, 70:456A, 1998.
Wu et al., *Biochem. Biophys. Res. Commun.*, 233(1):221-226, 1997.
Wu et al., *Biochim. Biophys. Acta*, 1466:315-327, 2000.
Yanagisawa et al., Lancet., 362:433-439, 2003.
Yang et al., *J. Agric. Food. Chem.*, 48:3990, 2000.
Zhong et al., *Clin. Chem. ACTA.*, 313:147, 2001.
Zimmerman et al., Methods Cell Biol., 89:361-390, 2008.
Zweigenbaum et al., *Anal. Chem.*, 71(13):2294-300, 1999.
Zweigenbaum et al., *J. Pharm. Biomed. Anal.*, 23(4):723-733, 2000.

What is claimed is:

1. A method of differentiating Spitz nevi from Spitzoid malignant melanoma comprising:
   (a) subjecting a skin lesion sample from a patient to mass spectrometry;
   (b) obtaining a mass spectrometric protein profile from said sample;
   (c) comparing said mass spectrometric protein profile to a known normal, Spitz nevi and/or Spitzoid malignant melanoma profile; and
   (d) classifying said lesion as a Spitz nevi or Spitzoid malignant melanoma based on the similarities and differences between said mass spectrometric protein profile and said known profile or profiles.

2. The method of claim 1, wherein said mass spectrometry is secondary ion mass spectrometry, laser desorption mass spectrometry, matrix assisted laser desorption mass spectrometry, electrospray mass spectrometry, or desorption electrospray ionization.

3. The method of claim 1, further comprising obtaining said sample from said patient.

4. The method of claim 1, further comprising making a treatment decision for said patient.

5. The method of claim 1, wherein said patient is identified as having Spitz nevi, then further comprising repeating steps (a)-(d) on said lesion in 6-12 months, 6-18 months, 6-24 months, 12-18 months, 12-24 months or 18-24 months.

6. The method of claim 1, wherein said patient is identified as having Spitzoid malignant melanoma, then further comprising treating said patient with chemotherapy, immunotherapy, toxin therapy or radiotherapy.

7. The method of claim 1, further comprising assessing one or more patient history parameters from said patient.

8. The method of claim 1, further comprising performing a mass spectrometric analysis of a known Spitz nevi and/or Spitzoid malignant melanoma lesion.

9. The method of claim 1, further comprising performing histologic analysis on said sample.

10. The method of claim 1, further comprising making a prediction of said patient's survival based on said classification.

11. The method of claim 1, wherein the skin lesion sample consists essentially of melanocytic components.

12. The method of claim 1, wherein the mass spectrometric profile comprises markers of vimentin and actin.

13. The method of claim 11, wherein the mass spectrometric profile comprises peptide peaks at m/z 976.5±0.2, m/z 1060.2±0.2, m/z 1410.7±0.2, m/z 1336.7±0.2 and m/z 1428.8±0.2 are examined.

14. The method of claim 1, wherein the skin lesion sample consists essentially of stromal components.

15. The method of claim 14, wherein the mass spectrometric profile comprises peptide peaks at m/z 713.2±0.2, m/z 1251.8±0.2, m/z 1287.7±0.2, m/z 1365.8±0.2, m/z 1428.8±0.2, m/z 1685.9±0.2, m/z 2519.3±0.2, m/z 2632.3±0.2, m/z 2773.3±0.2, m/z 3224.5±0.2, m/z 3287.1±0.2 and m/z 3411.8±0.2 are examined.

16. The method of claim 1, wherein both melanocytic and stromal components of said skin lesion sample are examined.

17. The method of claim 1, wherein said patient has previously had immunohistochemical analysis of said lesion.

18. The method of claim 17, wherein said previous immunohistochemical analysis in inidicated that said lesion was a Spitz nevus.

19. The method of claim 17, wherein said previous immunohistochemical analysis in inidicated that said lesion was a Spitzoid malignant melanoma.

20. The method of claim 1, further comprising immunohistochemical analysis on said skin lesion sample.

* * * * *